US008948848B2

(12) United States Patent
Merhi

(10) Patent No.: US 8,948,848 B2
(45) Date of Patent: Feb. 3, 2015

(54) ANGIOGRAPHY CATHETER

(75) Inventor: William M Merhi, Grand Rapids, MI (US)

(73) Assignee: Innovative Cardiovascular Solutions, LLC, Kalamazoo, MI (US)

( * ) Notice: Subject to any disclaimer, the term of this patent is extended or adjusted under 35 U.S.C. 154(b) by 249 days.

(21) Appl. No.: 13/311,265

(22) Filed: Dec. 5, 2011

(65) Prior Publication Data

US 2012/0179033 A1     Jul. 12, 2012

Related U.S. Application Data

(60) Provisional application No. 61/460,660, filed on Jan. 7, 2011.

(51) Int. Cl.
*A61B 6/00* (2006.01)
*A61B 5/05* (2006.01)
(Continued)

(52) U.S. Cl.
CPC . *A61F 2/013* (2013.01); *A61B 6/12* (2013.01); *A61B 18/1492* (2013.01); *A61B 2017/00243* (2013.01); *A61B 2019/5466* (2013.01);
(Continued)

(58) Field of Classification Search
USPC .......... 600/431, 434, 435, 424, 433; 606/200; 604/523, 529
See application file for complete search history.

(56) References Cited

U.S. PATENT DOCUMENTS 3,938,501 A    2/1976  Erikson
4,406,656 A    9/1983  Hattler et al.
(Continued)

FOREIGN PATENT DOCUMENTS

EP    0 129 634    1/1985
EP    0 154 403    9/1985
(Continued)

OTHER PUBLICATIONS

Nietlispach et al., "An Embolic Deflection Device for Aortic Valve Interventions," J. Am. Coll. Cardio. Intv.; Cardiovascular Interventions; vol. 3, No. 11, 2010: pp. 1133-1140. Downloaded from http://interventions.onlinejacc.org on Nov. 18, 2011.
(Continued)

*Primary Examiner* — Katherine Fernandez
(74) *Attorney, Agent, or Firm* — Honigman Miller Schwartz & Cohn LLP; Andrew N. Weber; Jonathan P. O'Brien

(57) ABSTRACT

Embolic protection devices and methods for capturing embolic debris. An embolic protection device includes a pigtail catheter having a lumen for housing a guidewire. The distal portion of the catheter has one or more apertures in fluid communication with the lumen and one or more radiopaque markers on the distal-most section. The device includes a self-expanding filter coupled to a side of the catheter and a movable outer sheath surrounding the catheter. The outer sheath holds the filter in a collapsed configuration when surrounding the filter. The outer sheath is proximally retracted to deploy the filter. A method of capturing embolic debris includes inserting a guidewire into a body lumen, tracking the device over the guidewire, retracting the guidewire, positioning the device using the radiopaque marker, retracting the outer sheath and deploying the filter, performing a procedure, and advancing the outer sheath to recapture the filter.

26 Claims, 20 Drawing Sheets

(51) Int. Cl.

| | |
|---|---|
| *A61M 29/00* | (2006.01) |
| *A61M 25/098* | (2006.01) |
| *A61F 2/01* | (2006.01) |
| A61B 6/12 | (2006.01) |
| A61B 18/14 | (2006.01) |
| A61B 17/00 | (2006.01) |
| A61B 19/00 | (2006.01) |
| A61F 2/24 | (2006.01) |

(52) U.S. Cl.

CPC ......... *A61F2/2433* (2013.01); *A61F 2002/018* (2013.01); *A61F 2250/0098* (2013.01); *A61F 2230/0006* (2013.01); *A61F 2230/0008* (2013.01); *A61F 2230/0067* (2013.01); *A61F 2230/008* (2013.01)

USPC ........... 600/435; 600/424; 600/431; 606/200; 604/529

(56) References Cited

U.S. PATENT DOCUMENTS

| | | | |
|---|---|---|---|
| 4,425,908 A | 1/1984 | Simon | |
| 4,531,933 A | 7/1985 | Norton et al. | |
| 4,601,713 A | 7/1986 | Fuqua | |
| 4,671,795 A | 6/1987 | Mulchin | |
| 4,694,838 A | 9/1987 | Wijayarthna et al. | |
| 4,710,181 A | 12/1987 | Fuqua | |
| 4,735,620 A | 4/1988 | Ruiz | |
| 4,738,666 A | 4/1988 | Fuqua | |
| 4,878,495 A | 11/1989 | Grayzel | |
| 4,958,634 A | 9/1990 | Jang | |
| 4,961,731 A | 10/1990 | Bodicky et al. | |
| 4,986,814 A | 1/1991 | Burney et al. | |
| 5,106,368 A | 4/1992 | Uldall et al. | |
| 5,163,431 A | 11/1992 | Griep | |
| 5,180,364 A | 1/1993 | Ginsburg | |
| 5,192,286 A | 3/1993 | Phan et al. | |
| 5,201,723 A | 4/1993 | Quinn | |
| 5,221,253 A | 6/1993 | Coll | |
| 5,320,605 A | 6/1994 | Sahota | |
| 5,421,832 A | 6/1995 | Lefebvre | |
| 5,472,418 A | 12/1995 | Palestrant | |
| 5,474,537 A | 12/1995 | Solar | |
| 5,573,508 A | 11/1996 | Thornton | |
| 5,658,296 A | 8/1997 | Bates et al. | |
| 5,735,831 A | 4/1998 | Johnson et al. | |
| 5,738,667 A | 4/1998 | Solar | |
| 5,779,716 A | 7/1998 | Cano et al. | |
| 5,795,322 A | 8/1998 | Boudewijn | |
| 5,807,318 A * | 9/1998 | St. Goar et al. | 604/508 |
| 5,810,874 A | 9/1998 | Lefebvre | |
| 5,814,064 A | 9/1998 | Daniel et al. | |
| 5,827,324 A | 10/1998 | Cassell et al. | |
| 5,910,154 A | 6/1999 | Tsugita et al. | |
| 5,947,995 A | 9/1999 | Samuels | |
| 5,954,745 A | 9/1999 | Gertler et al. | |
| 6,001,118 A | 12/1999 | Daniel et al. | |
| 6,053,932 A | 4/2000 | Daniel et al. | |
| 6,059,814 A | 5/2000 | Ladd | |
| 6,129,739 A | 10/2000 | Khosravi | |
| 6,142,987 A | 11/2000 | Tsugita | |
| 6,152,946 A | 11/2000 | Broome et al. | |
| 6,168,579 B1 | 1/2001 | Tsugita | |
| 6,168,604 B1 | 1/2001 | Cano | |
| 6,179,859 B1 | 1/2001 | Bates et al. | |
| 6,179,861 B1 | 1/2001 | Khosravi et al. | |
| 6,183,492 B1 | 2/2001 | Hart et al. | |
| 6,190,357 B1 | 2/2001 | Ferrari et al. | |
| 6,203,561 B1 | 3/2001 | Ramee et al. | |
| 6,214,026 B1 | 4/2001 | Lepak et al. | |
| 6,245,087 B1 | 6/2001 | Addis | |
| 6,245,089 B1 | 6/2001 | Daniel et al. | |
| 6,264,663 B1 | 7/2001 | Cano | |
| 6,277,138 B1 | 8/2001 | Levinson et al. | |
| 6,277,139 B1 | 8/2001 | Levinson et al. | |
| 6,290,710 B1 | 9/2001 | Cryer et al. | |
| 6,336,934 B1 | 1/2002 | Gilson et al. | |
| 6,346,116 B1 | 2/2002 | Brooks et al. | |
| 6,361,545 B1 | 3/2002 | Macoviak et al. | |
| 6,371,970 B1 | 4/2002 | Khosravi et al. | |
| 6,371,971 B1 | 4/2002 | Tsugita et al. | |
| 6,395,014 B1 | 5/2002 | Macoviak et al. | |
| 6,398,756 B2 | 6/2002 | Peterson et al. | |
| 6,425,909 B1 | 7/2002 | Dieck et al. | |
| 6,527,746 B1 | 3/2003 | Oslund et al. | |
| 6,530,939 B1 | 3/2003 | Hopkins et al. | |
| 6,537,294 B1 | 3/2003 | Boyle et al. | |
| 6,540,722 B1 | 4/2003 | Boyle et al. | |
| 6,544,279 B1 | 4/2003 | Hopkins et al. | |
| 6,589,263 B1 | 7/2003 | Hopkins et al. | |
| 6,595,967 B2 | 7/2003 | Kramer | |
| 6,605,074 B2 | 8/2003 | Zadno-Azizi et al. | |
| 6,645,224 B2 | 11/2003 | Gilson et al. | |
| 6,656,202 B2 | 12/2003 | Papp et al. | |
| 6,660,021 B1 | 12/2003 | Palmer et al. | |
| 6,692,512 B2 | 2/2004 | Jang | |
| 6,740,061 B1 | 5/2004 | Oslund et al. | |
| 6,887,256 B2 * | 5/2005 | Gilson et al. | 606/200 |
| 6,936,059 B2 | 8/2005 | Belef | |
| 6,939,361 B1 | 9/2005 | Kleshinski | |
| 6,951,555 B1 | 10/2005 | Suresh et al. | |
| 6,969,396 B2 | 11/2005 | Krolik et al. | |
| 6,989,027 B2 | 1/2006 | Allen et al. | |
| 7,004,176 B2 | 2/2006 | Lau | |
| 7,014,647 B2 | 3/2006 | Brady et al. | |
| 2002/0095174 A1 | 7/2002 | Tsugita et al. | |
| 2002/0161394 A1 | 10/2002 | Macoviak et al. | |
| 2003/0233115 A1 | 12/2003 | Eversull et al. | |
| 2004/0193207 A1 | 9/2004 | Boismier | |
| 2004/0220521 A1 | 11/2004 | Barbut | |
| 2004/0249409 A1 | 12/2004 | Krolik et al. | |
| 2005/0101987 A1 | 5/2005 | Salahieh | |
| 2005/0131438 A1 | 6/2005 | Cohn | |
| 2005/0131449 A1 | 6/2005 | Salahieh et al. | |
| 2005/0288631 A1 | 12/2005 | Lewis et al. | |
| 2006/0195138 A1 | 8/2006 | Goll et al. | |
| 2007/0198051 A1 | 8/2007 | Clubb et al. | |
| 2009/0062840 A1 | 3/2009 | Angel | |
| 2010/0312268 A1 | 12/2010 | Belson | |
| 2010/0324554 A1 | 12/2010 | Gifford et al. | |

FOREIGN PATENT DOCUMENTS

| | | |
|---|---|---|
| EP | 0 453 008 | 10/1991 |
| EP | 2 166 958 | 1/2009 |
| WO | WO 00/12169 | 3/2000 |
| WO | WO 03/090834 | 11/2003 |
| WO | WO 2010/026240 | 3/2010 |

OTHER PUBLICATIONS

Edwards Lifesciences LLC, Edwards Protection Cannulae, "EMBOL-X Glide Protection System," Brochure, 2010.
International Search Report and Written Opinion for Application No. PCT/US2011/67440 dated Apr. 27, 2012.

* cited by examiner

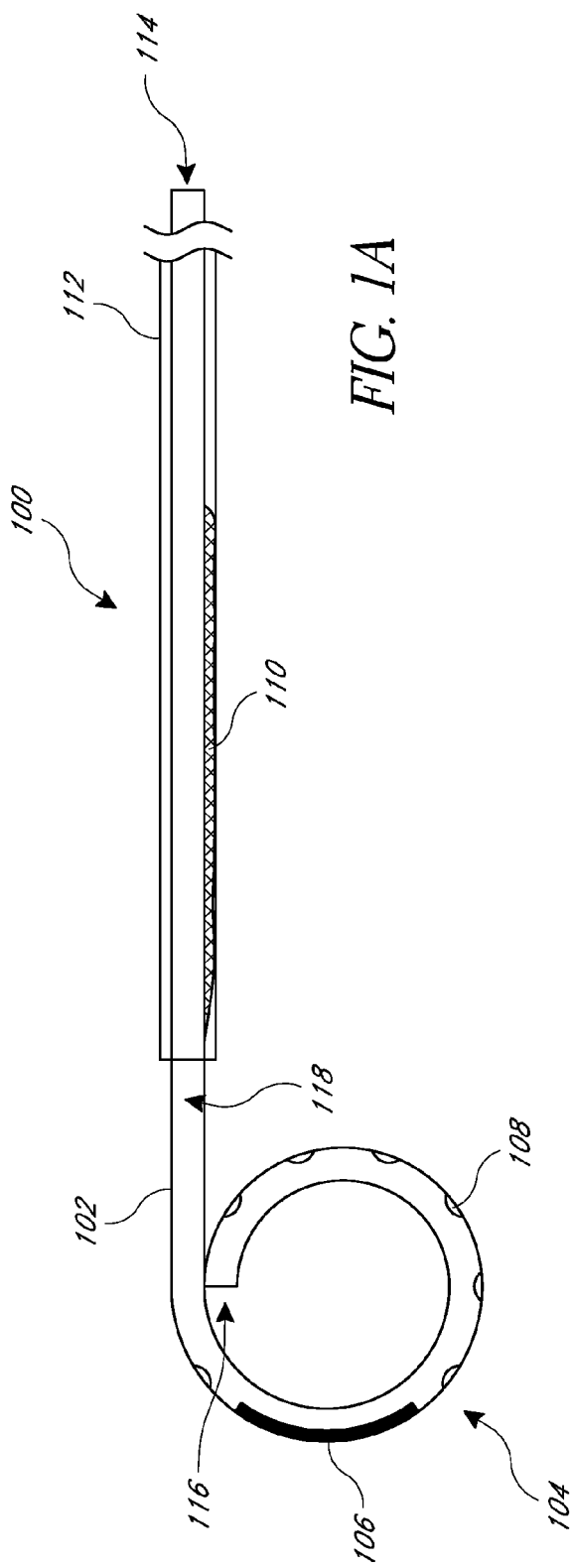
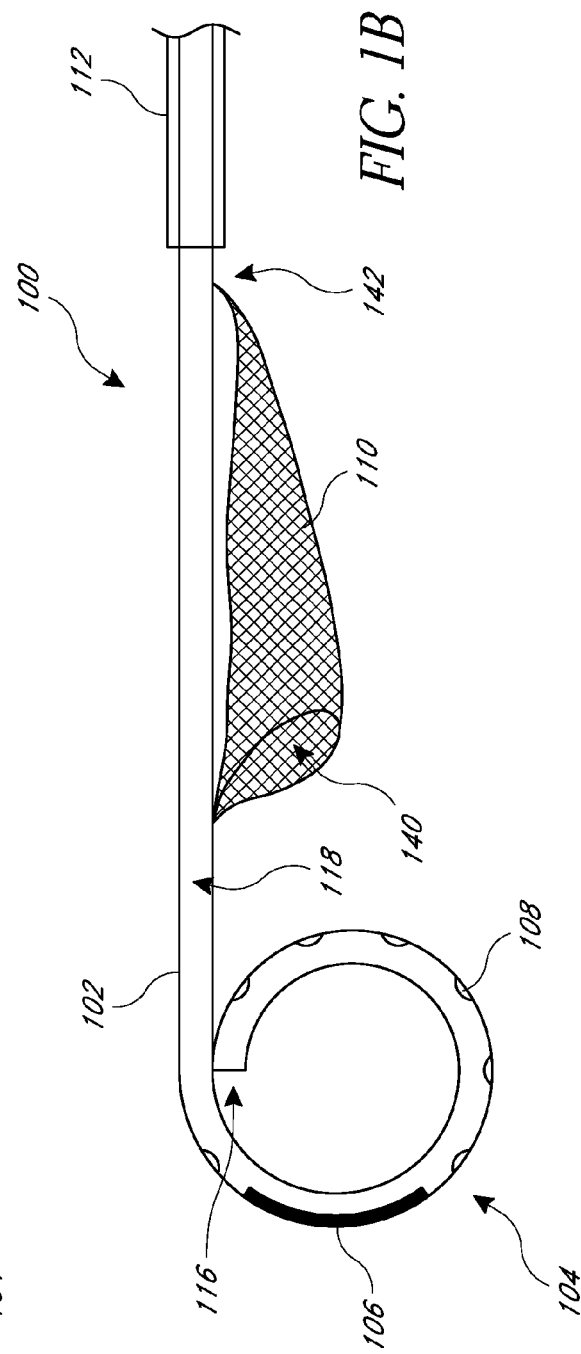

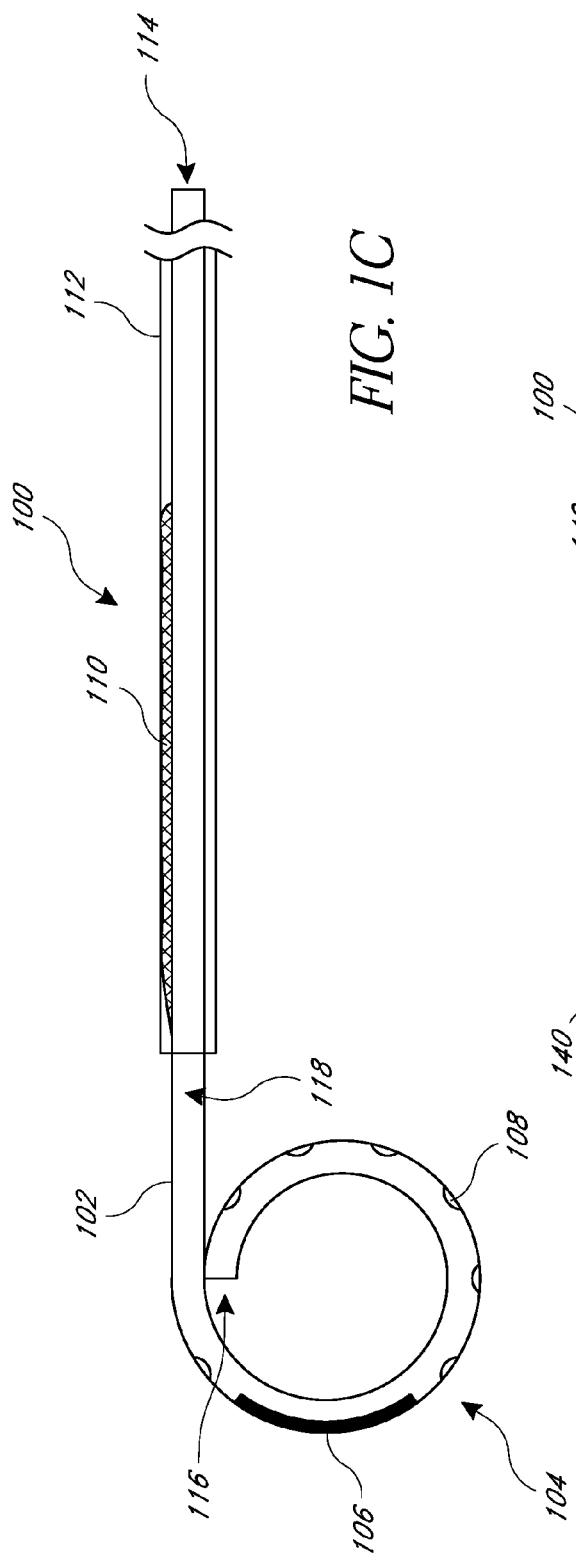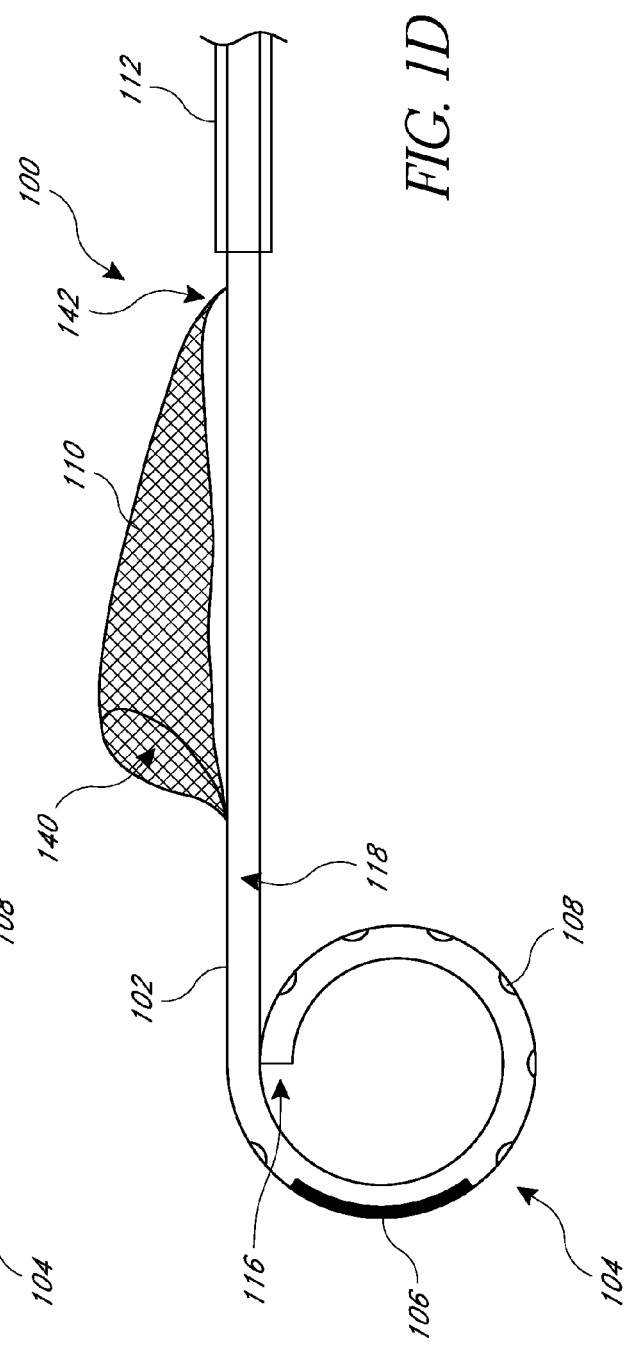

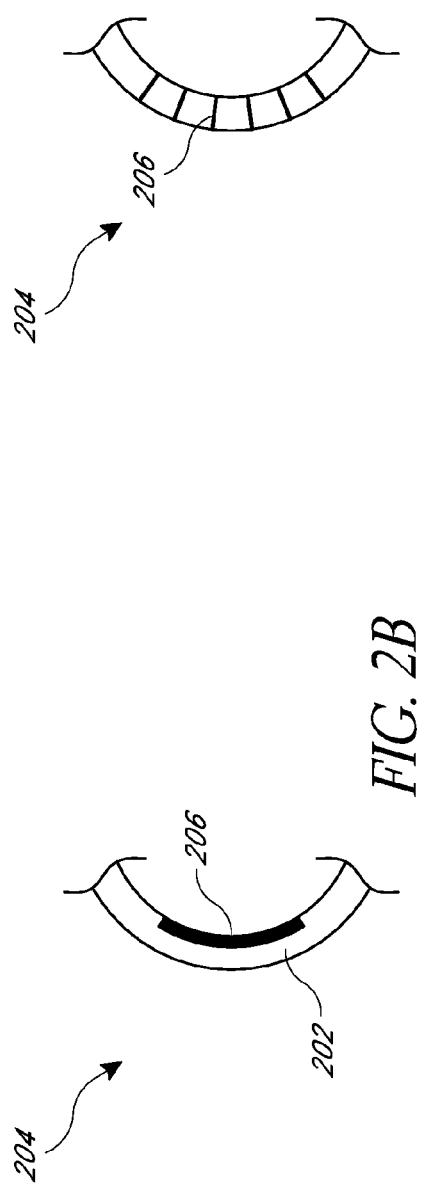
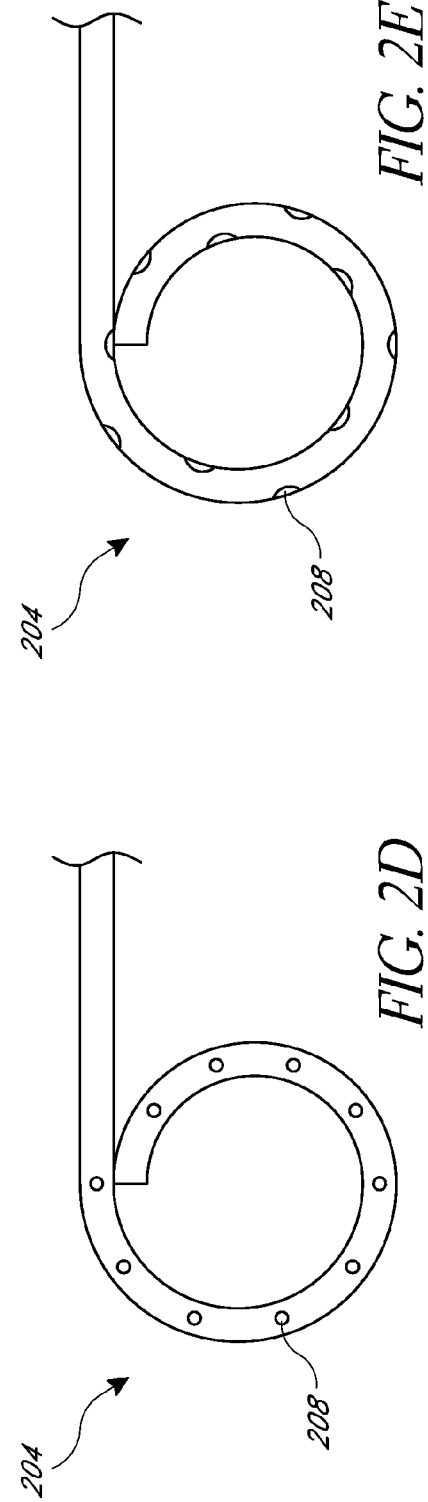

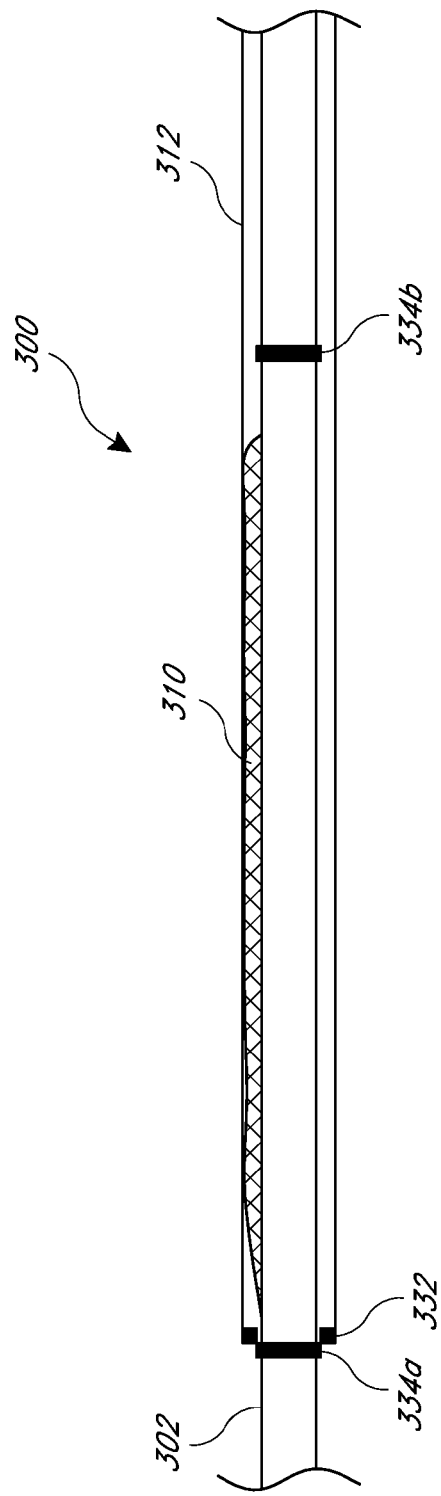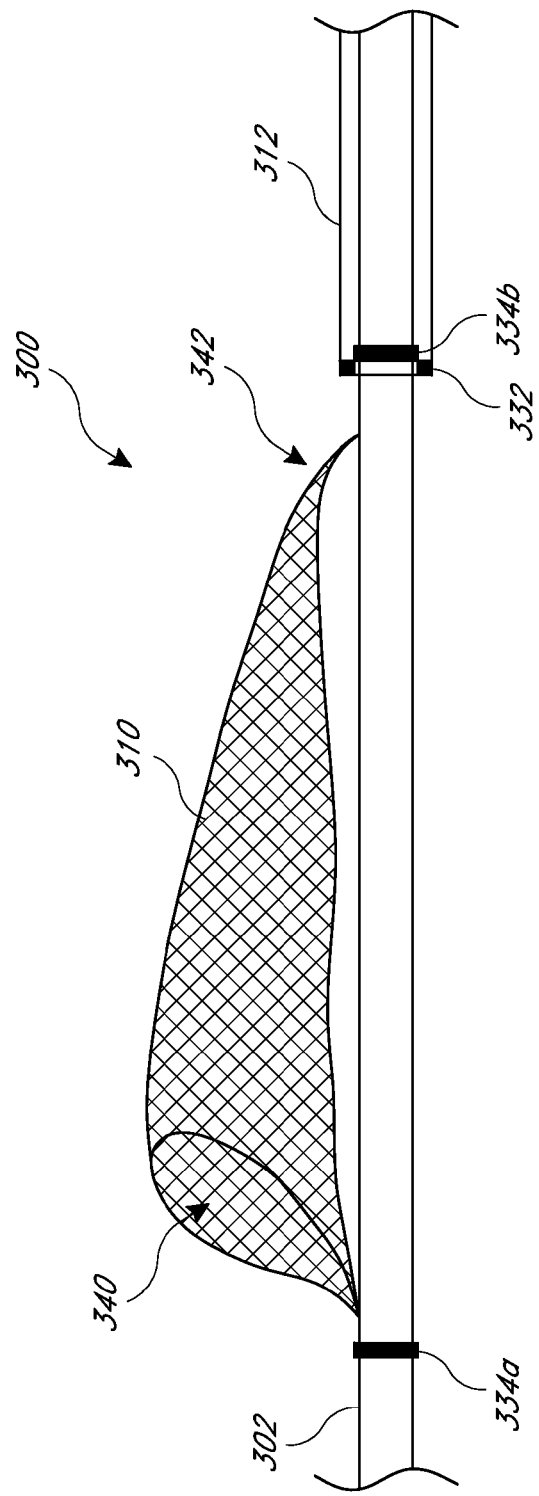

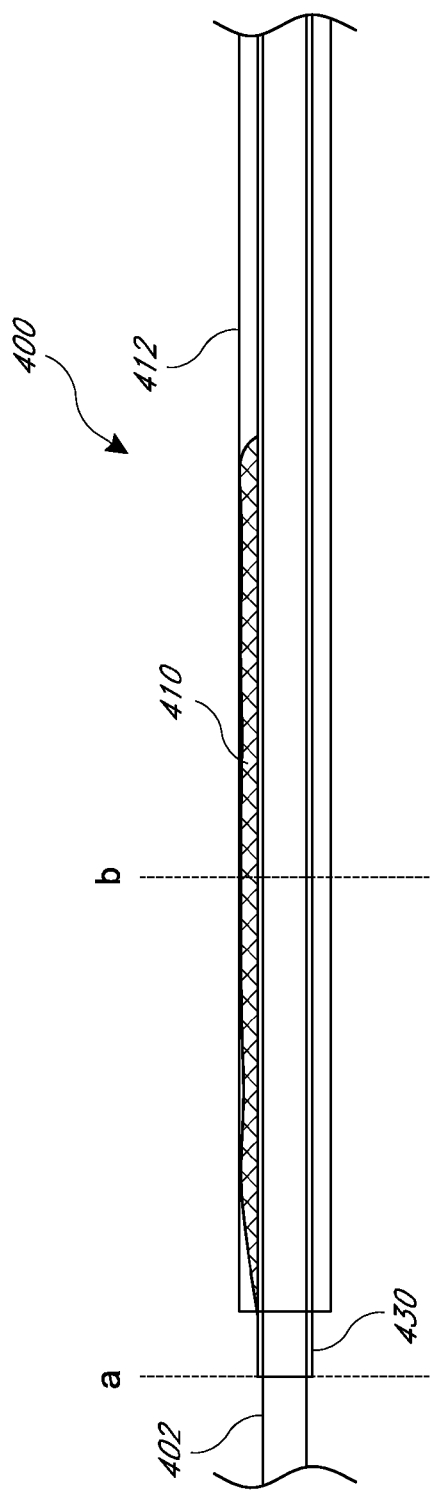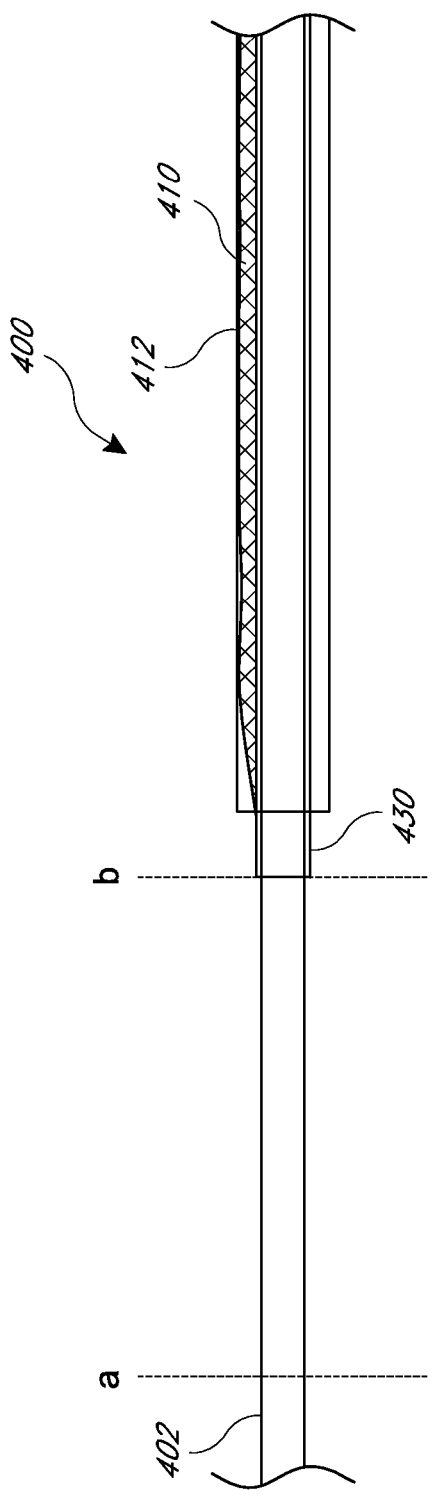

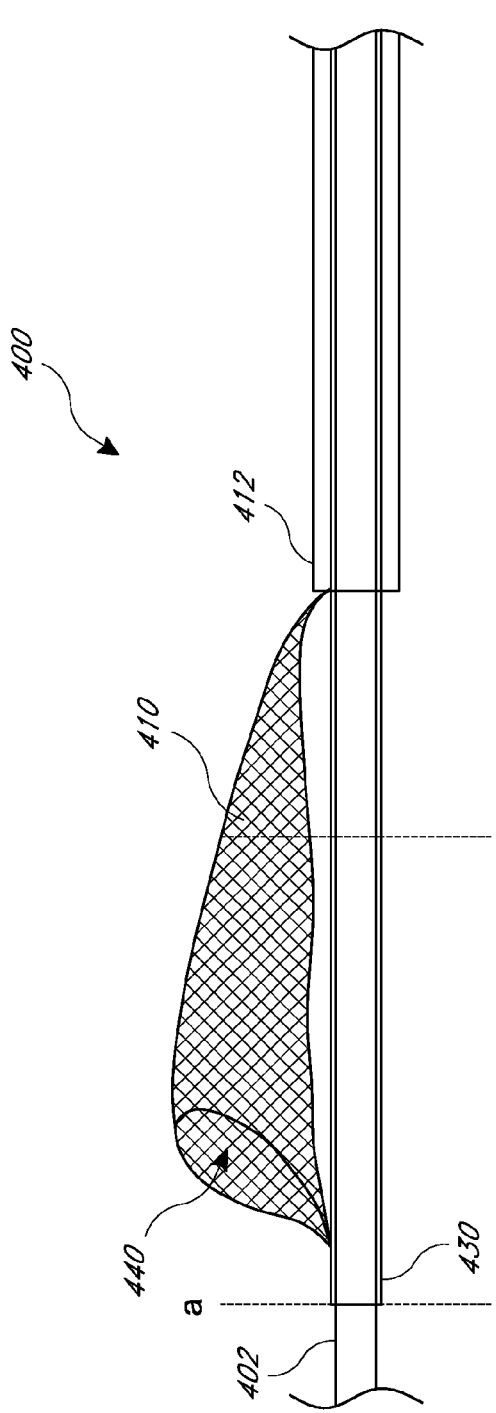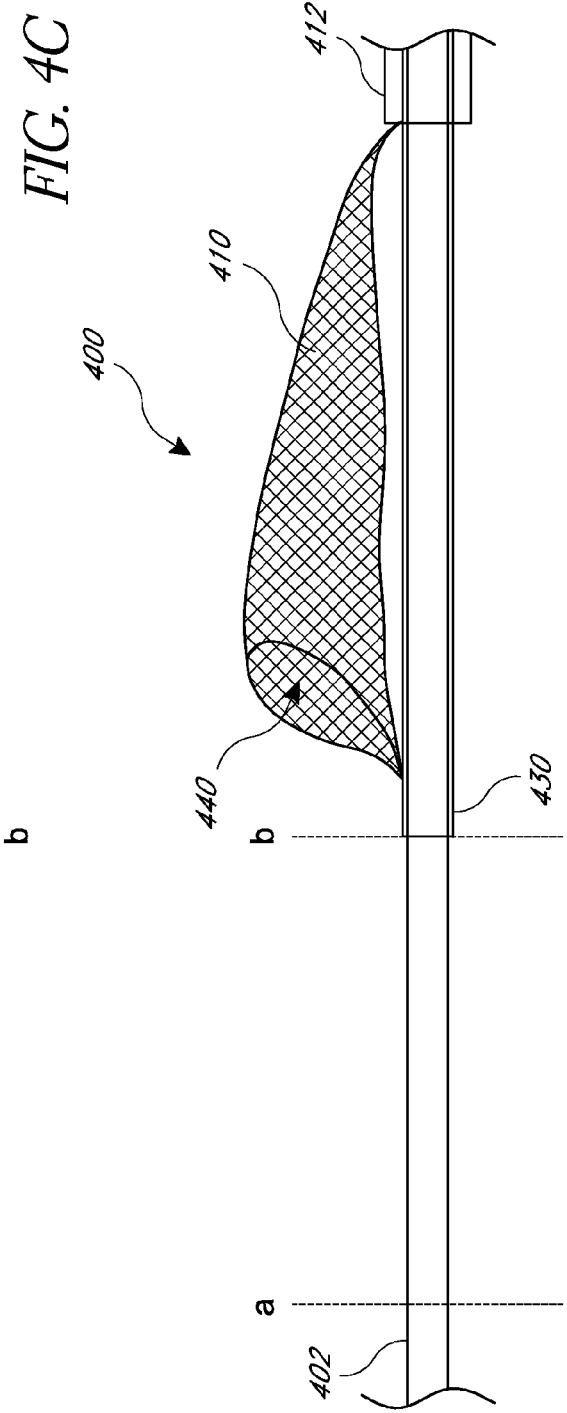

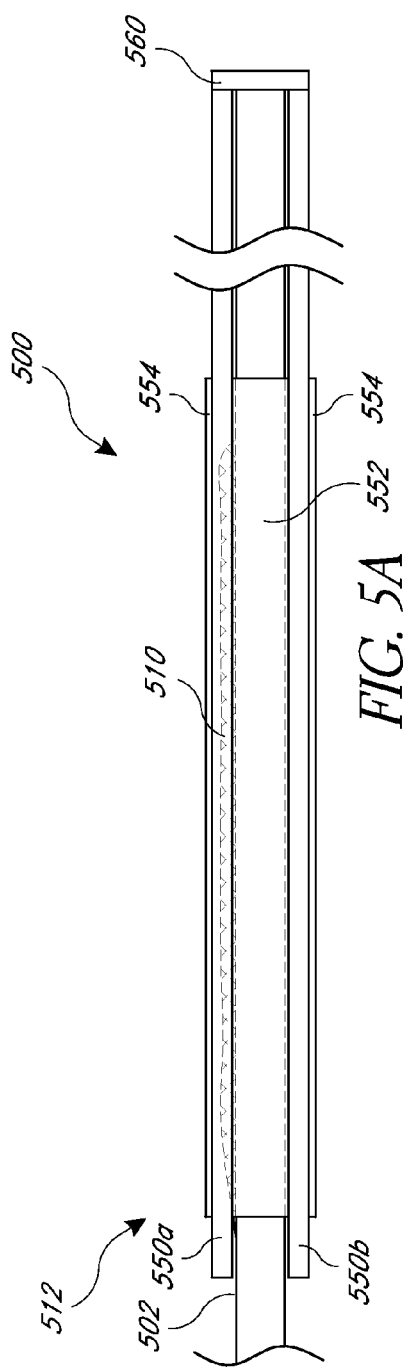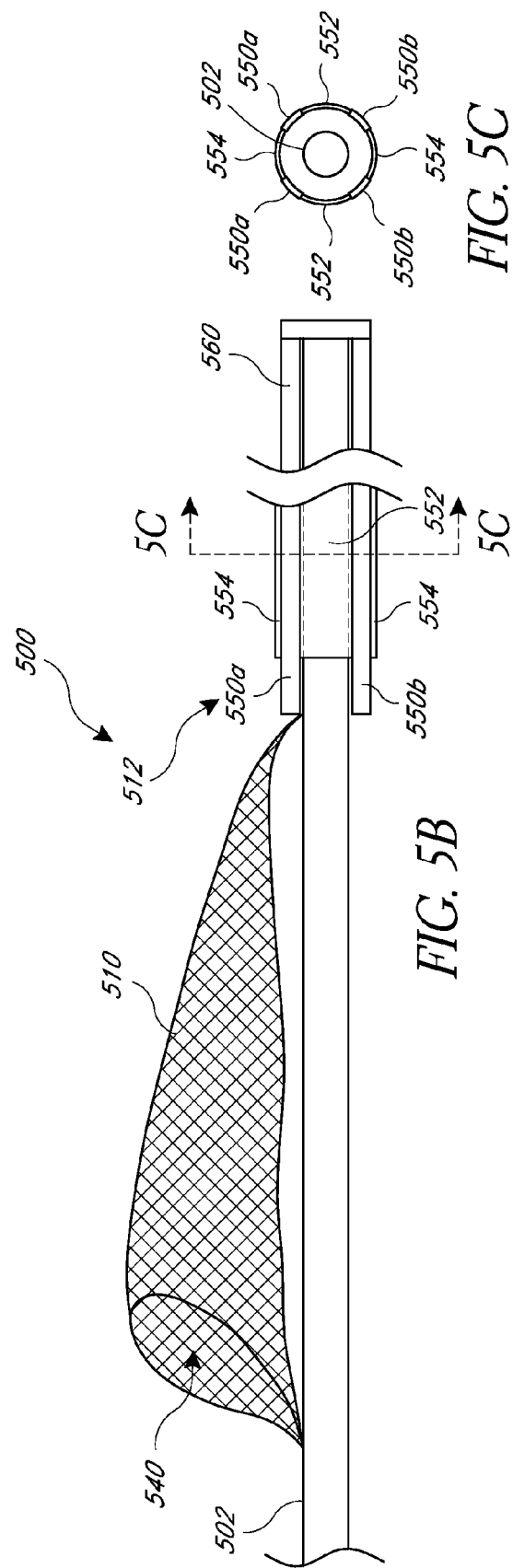

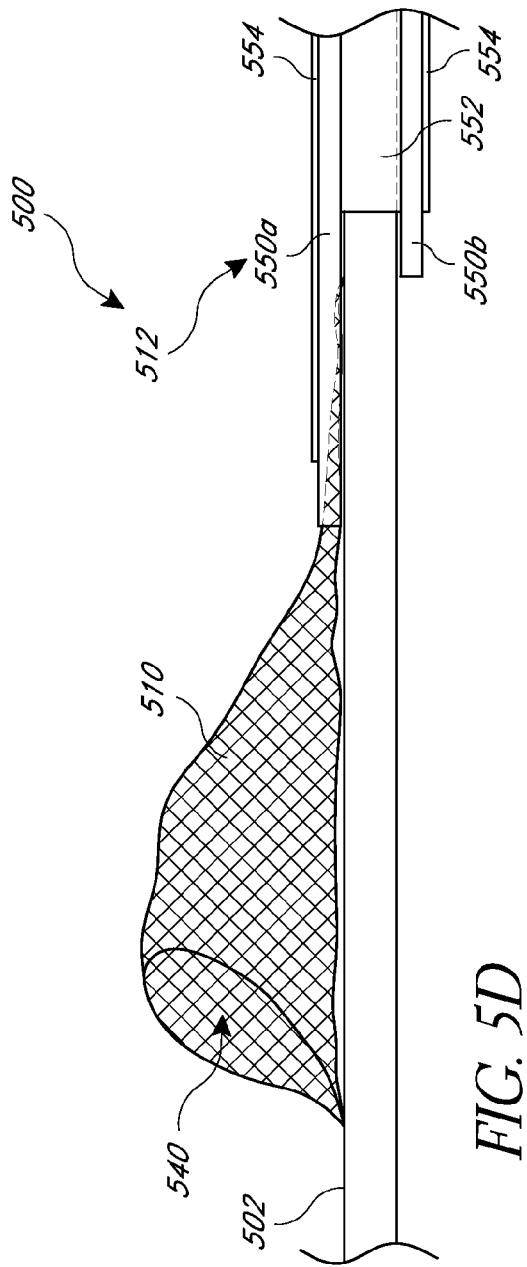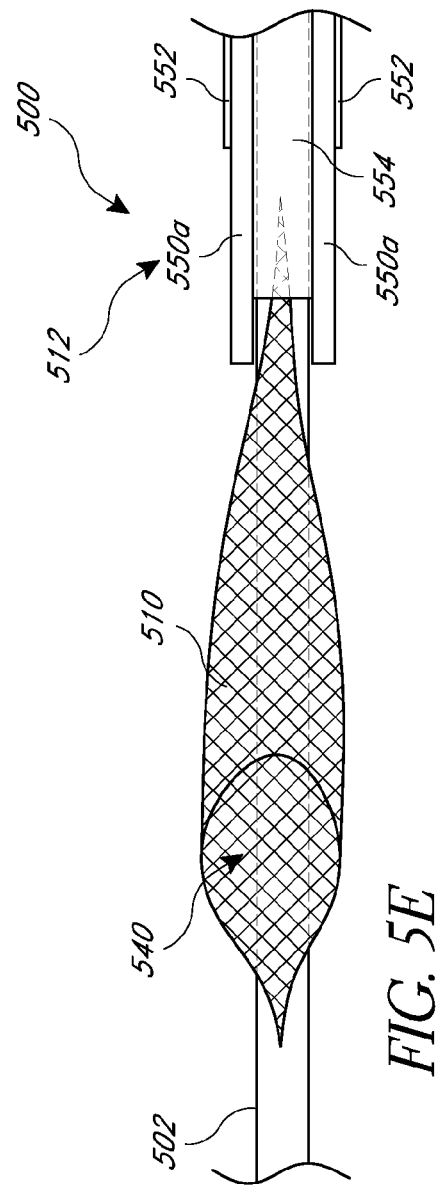
FIG. 5D
FIG. 5E

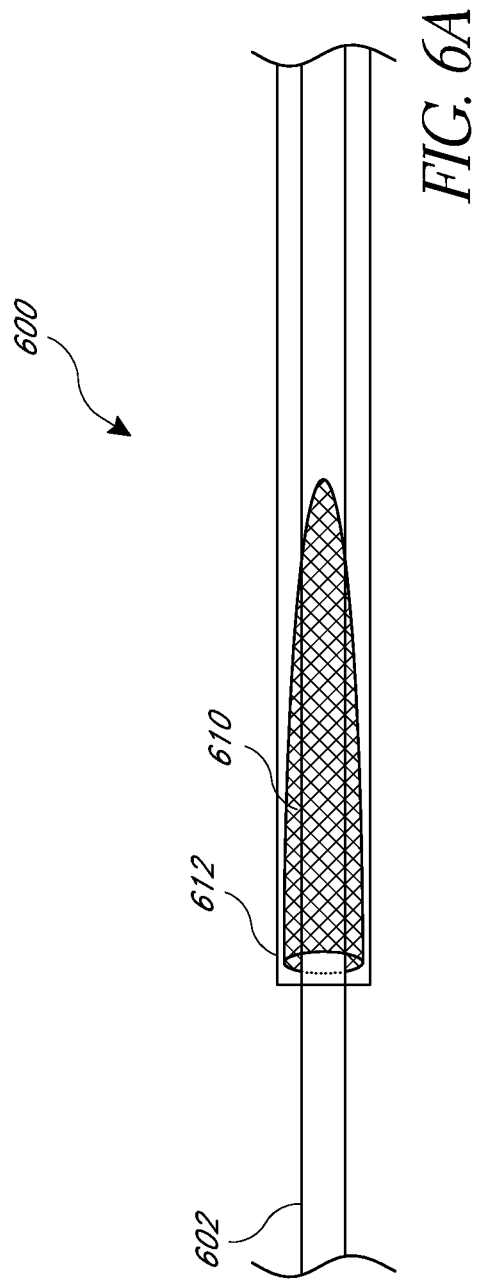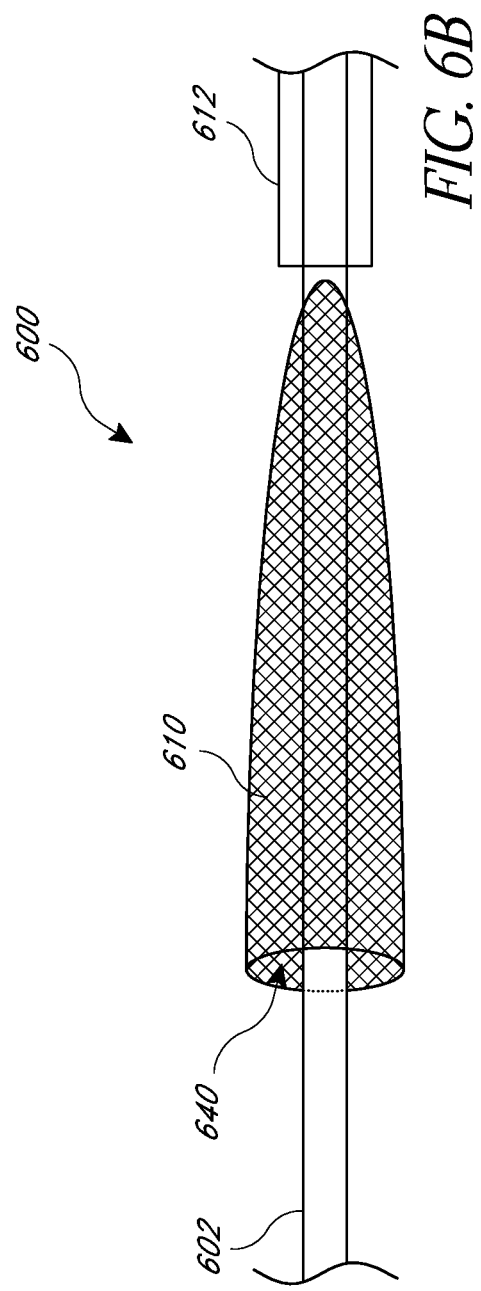

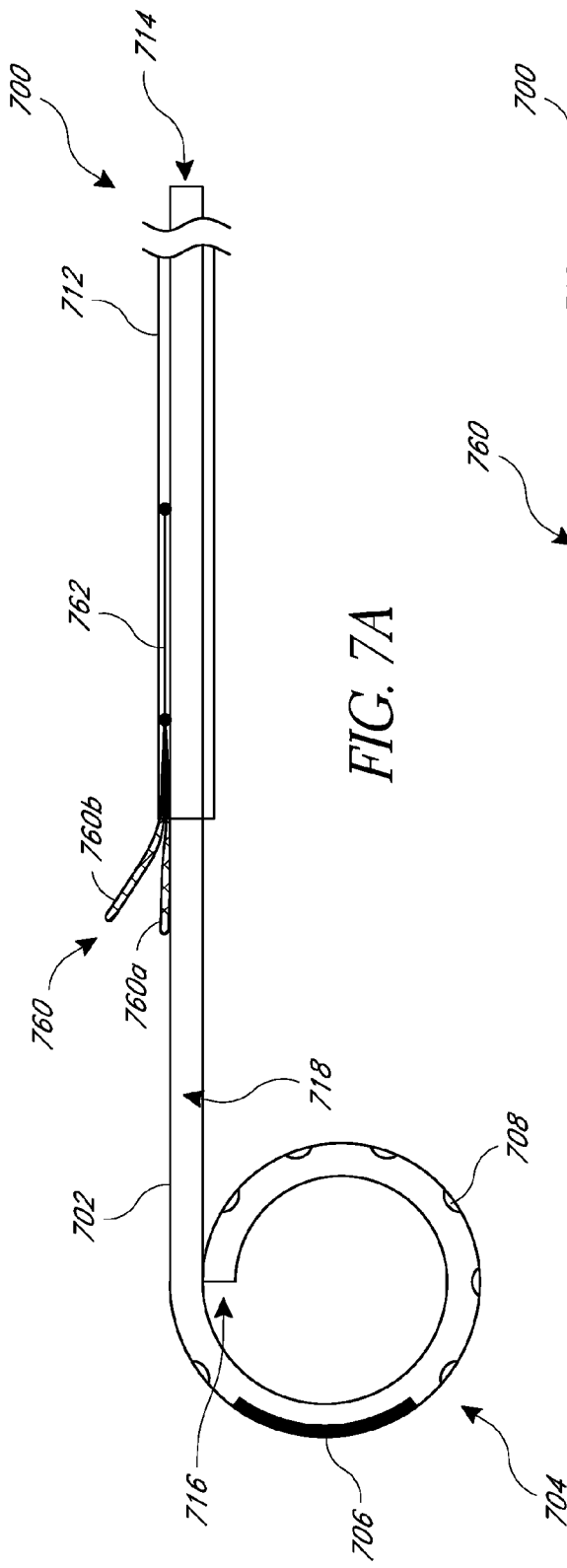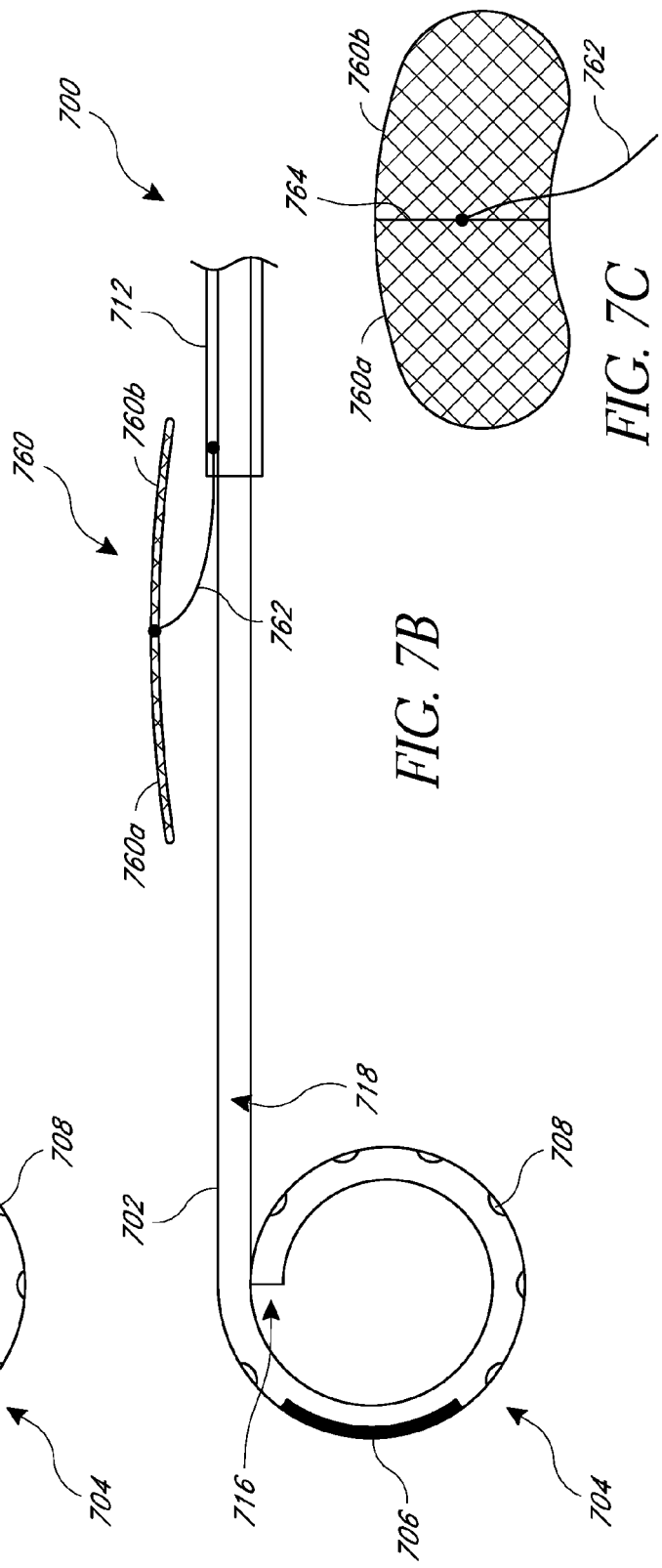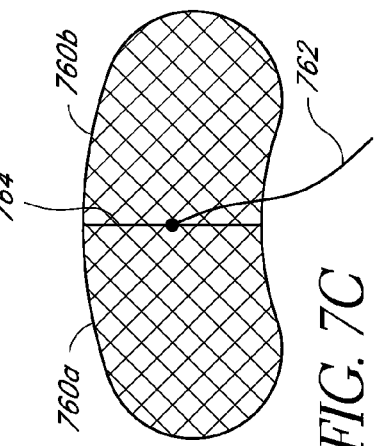
FIG. 7A
FIG. 7B
FIG. 7C

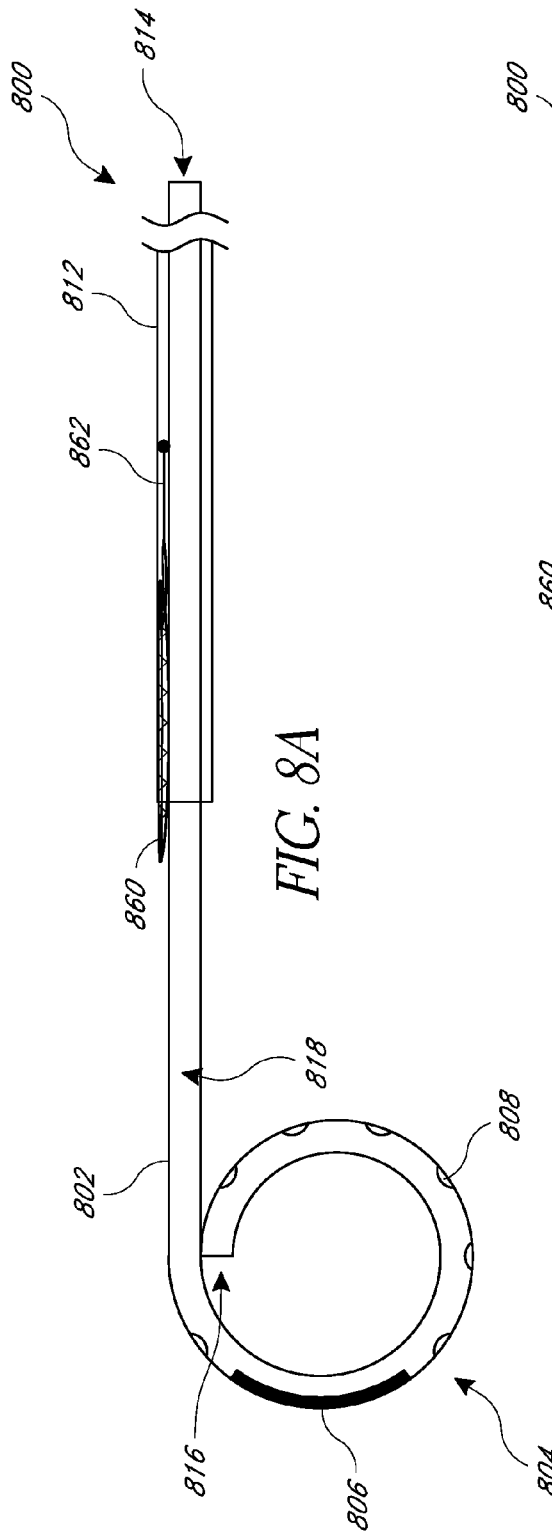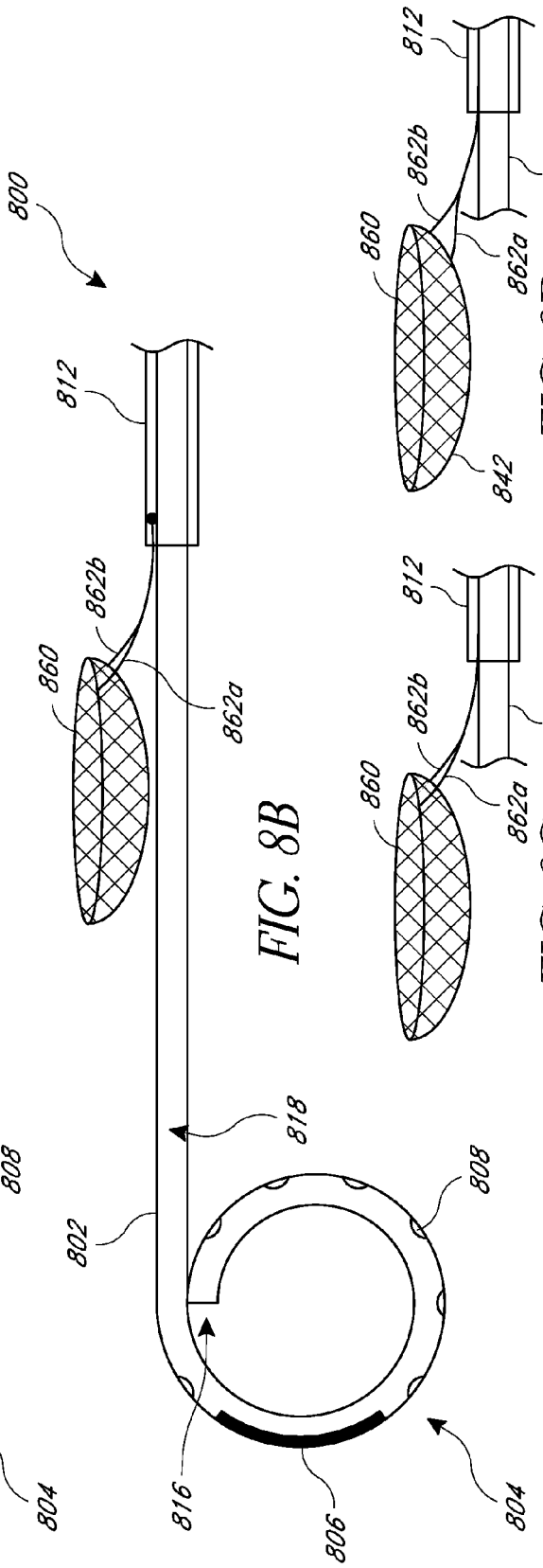

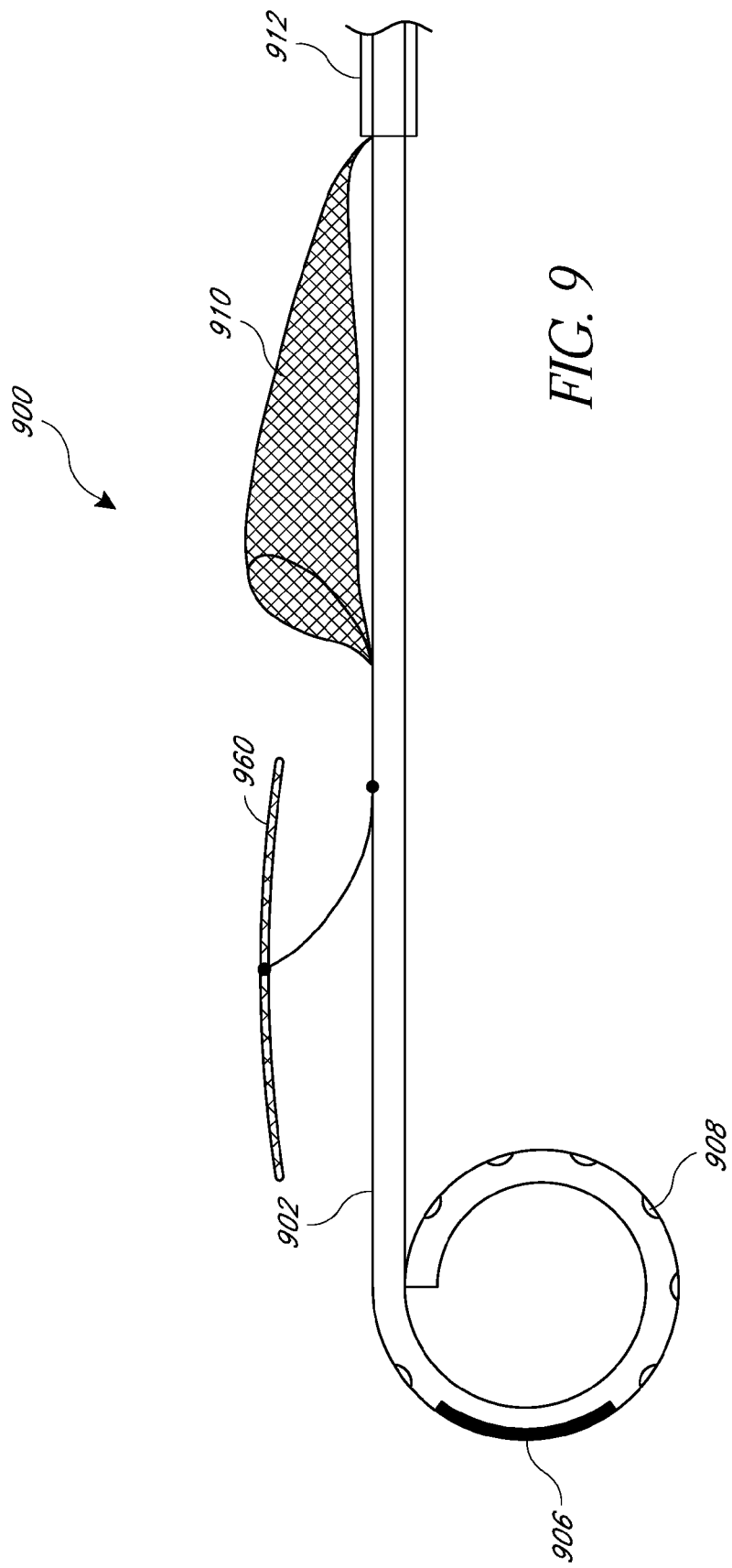

ANGIOGRAPHY CATHETER

CROSS-REFERENCE TO RELATED APPLICATIONS

This application claims priority benefit of U.S. Provisional Patent Application No. 61/460,660, filed Jan. 7, 2011, the entirety of which is hereby incorporated by reference.

BACKGROUND

1. Field

The present application generally relates to devices and methods for locating the proper position to perform a cardiac procedure and/or capturing embolic debris during a cardiac procedure.

2. Description of the Related Art

During percutaneous cardiac procedures, precise positioning of various instruments and devices can be important. For example, when performing a percutaneous valve replacement procedure, the valve is generally placed no more than 4-6 millimeters (mm) below the lower border of the aortic annulus. Placing the valve prosthesis too low or too high can result in severe leaking of the valve, which in some cases can be fatal. Therefore, it can be important to identify the lower border of the annulus to use as a reference point. A pigtail catheter may be used to inject a contrast agent to allow for visualization for proper positioning. Pigtail catheters may include a coiled distal portion and a plurality of small holes in the catheter side walls. The small holes allow for the introduction of contrast materials into the body for imaging purposes or drainage of fluids from the body. The coiled distal portion helps hold the catheter is place and can slow the flow of contrast fluids from the catheter lumen to avoid causing internal injuries or poor imaging results.

A potential complication of cardiac procedures such as valve replacement and repair is that plaque, calcium, and/or thrombi in the vessels, valves, and/or cardiac chambers can be dislodged and cause an embolism. Indeed, 2.9%-6.7% of patients undergoing transfemroal transcatheter aortic-valve implantation (TAVI) have a stroke within 30 days, and even more (4.5%-10.6%) have a stroke within a year, often leading to death. There are a few devices on the market designed to protect the carotid arteries from emboli; however, these devices have various disadvantages. For example, the Embrella Embolic Deflector®, available from Edwards Lifesciences of Irvine, Calif., deflects emboli from the carotid arteries into the descending aorta, but does not trap the emboli, so there is a risk of embolisms in other areas of the body. The EMBOL-X®, also available from Edwards Lifesciences, employs a filtering screen, but it is designed for use in open heart procedures. Additionally, the use of multiple devices, for example a catheter for visualization and a separate filter device, lengthens the procedure time and increases the risk of complications to the patient.

SUMMARY

A vascular device includes a pigtail and/or an embolic protection device. A pigtail is configured to curl at the distal end of the catheter, for example when there is no guidewire in a lumen of the catheter. The pigtail includes a radiopaque marker viewable on x-rays or other radiation devices. The radiopaque marker is on the distal-most section of the curled pigtail in the form of a longitudinal marker, multiple bands, etc. The pigtail may include apertures to dispense drugs and/or contrast agents through the lumen. An embolic protection device includes a self-expanding filter coupled to the catheter and an outer sheath movable with respect to the filter and the catheter. The outer sheath holds the filter in a collapsed configuration when surrounding the filter and is proximally retracted to deploy the filter. The outer sheath may recapture the filter and any debris captured therein by being distally advanced. The filter and outer sheath might both be movable with respect to the catheter, for example to be able to move the filter longitudinally without having to move the entire catheter longitudinally. The combination of the pigtail and the embolic protection device in the same vascular device may provide the benefits of both devices individually, as well as a synergistic effect. For example, expansion of the filter may help to anchor the pigtail into position to provide a more accurate position of the catheter than if the position of the pigtail could be influenced by blood flow, tissue movement, etc. In a valve replacement procedure, anchoring of the pigtail and more accurate positioning of the catheter may in turn help ensure that the valve prosthesis is properly positioned and stabilized. For another example, the position of the pigtail may ensure that the filter is being properly positioned.

To use these types of devices, a guidewire is inserted through the patient's skin and into a body lumen such as a femoral, radial, or brachial artery and steered near a target site. The guidewire is inserted into a lumen of the device, and the device is pushed or tracked over the guidewire to the target site. When the guidewire is retracted from at least the distal portion of the catheter, the pigtail assumes the generally arcuate shape. The radiopaque marker on the pigtail is used to visualize and position the catheter. Once the catheter is in position, the outer sheath is retracted to deploy the filter spanning across the vessel. The user can then perform a procedure such as valve replacement, valve repair, radio frequency ablation, etc. When the procedure is completed, the outer sheath is advanced to recapture the filter and any debris trapped in the filter. The device is then retracted, with the pigtail being atraumatic to vessels during retraction.

In some embodiments, an embolic protection device comprises a catheter having a proximal end a distal end. A lumen extends from the proximal end of the catheter to the distal end of the catheter. The lumen is configured to house a guidewire. A distal portion of the catheter is configured to assume a generally arcuate shape that is at least a semi-circle. The distal portion of the catheter includes a longitudinally-extending radiopaque marker configured to be arcuate and on a distal-most section of the catheter when the distal portion is in the generally arcuate shape. The device further comprises a self-expanding embolic filter coupled to the catheter proximal to the distal portion. The embolic filter has a generally conical shape extending between a distal opening and a closed proximal end. The device also includes a deployment mechanism circumferentially disposed around at least a portion of the catheter and longitudinally movable with respect to the catheter. The deployment mechanism is configured to contain the embolic filter in a collapsed configuration. The embolic filter is configured to self-expand when the deployment mechanism is longitudinally proximally retracted.

In some embodiments, an angiography catheter comprises a catheter having a proximal end and a distal end. A lumen extends from the proximal end of the catheter to the distal end of the catheter and is configured to house a guidewire. A distal portion of the catheter is configured to assume a generally arcuate shape that is at least a semi-circle. The distal portion of the catheter includes a longitudinally-extending radiopaque marker configured to be arcuate and on a distal-most section of the catheter when the distal portion is in the generally arcuate shape.

In some embodiments, an embolic protection device comprises a catheter having a proximal end and a distal end. The device further comprises a self-expanding embolic filter coupled to a side of the catheter. The embolic filter has a generally conical shape and extends between a distal opening and a closed proximal end. The device also includes an outer sheath that is longitudinally movable with respect to the embolic filter. The outer sheath is configured to contain the embolic filter in a collapsed state when the sheath is at least partially around the embolic filter. The embolic filter is configured to self-expand when the outer sheath is longitudinally proximally retracted.

In some embodiments, an embolic protection device comprises a catheter having a proximal end a distal end. A lumen extends from the proximal end of the catheter to the distal end of the catheter. The lumen is configured to house a guidewire. A distal portion of the catheter is configured to assume a generally arcuate shape that is at least a semi-circle. The distal portion of the catheter includes a longitudinally-extending radiopaque marker configured to be arcuate and on a distal-most section of the catheter when the distal portion is in the generally arcuate shape. The device further comprises a self-expanding deflector coupled to a side of the catheter and having a longitudinal axis parallel to a longitudinal axis of the catheter. The device also includes a deployment mechanism circumferentially disposed around at least a portion of the catheter and longitudinally movable with respect to the catheter. The deployment mechanism is configured to contain the deflector in a collapsed configuration. The deflector is configured to self-expand when the deployment mechanism is longitudinally moved.

In some embodiments, an embolic protection device comprises a catheter having a proximal end and a distal end. The device comprises a deflector coupled to a side of the catheter. The deflector has a longitudinal axis parallel to a longitudinal axis of the catheter. The device also includes an outer sheath that is longitudinally movable with respect to the deflector. The outer sheath is configured to contain the deflector in a collapsed state when the sheath is at least partially around the deflector. The deflector is configured to self-expand when the outer sheath is longitudinally moved.

In some embodiments, an embolic protection device comprises a catheter having a proximal end and a distal end. The device comprises a deflector coupled to a side of the catheter. The deflector has a longitudinal axis parallel to a longitudinal axis of the catheter. The device further comprises a self-expanding embolic filter coupled to the catheter. The embolic filter has a generally conical shape and extends between a distal opening and a closed proximal end. The device also includes an outer sheath that is longitudinally movable with respect to the deflector and embolic filter. The outer sheath is configured to contain the deflector and embolic filter in a collapsed state when the sheath is at least partially around the deflector and embolic filter. The deflector and embolic filter are configured to self-expand when the outer sheath is longitudinally moved.

In some embodiments, a method of capturing embolic debris comprises inserting a distal end of an angiography catheter into a body lumen by tracking a lumen of the catheter over a guidewire percutaneously inserted into the body lumen. The angiography catheter has a proximal end and a distal end, and the lumen extends from the proximal end to the distal end. A distal portion of the angiography catheter includes a longitudinally-extending radiopaque marker. A self-expanding embolic filter is attached to a side of the catheter proximal to the distal portion. The angiography catheter also includes an outer sheath that contains the embolic filter in a collapsed configuration. When the guidewire is removed from the distal portion of the catheter, the distal portion assumes a generally arcuate shape. The method further comprises positioning the catheter by visualizing the radiopaque marker with an imaging technique and longitudinally proximally retracting the outer sheath, allowing the embolic filter to assume an expanded, deployed configuration having a distal opening substantially spanning the body lumen.

For purposes of summarizing the disclosure and the advantages achieved over the prior art, certain objects and advantages are described herein. Of course, it is to be understood that not necessarily all such objects or advantages need to be achieved in accordance with any particular embodiment. Thus, for example, those skilled in the art will recognize that the disclosure may be embodied or carried out in a manner that achieves or optimizes one advantage or group of advantages as taught or suggested herein without necessarily achieving other objects or advantages as may be taught or suggested herein.

All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects, and advantages of the present disclosure are described with reference to the drawings of certain embodiments, which are intended to schematically illustrate certain embodiments and not to limit the invention.

FIGS. 1A and 1B show partial side views of an example embodiment of an embolic protection device;

FIGS. 1C and 1D show partial side views of another example embodiment of an embolic protection device;

FIGS. 2B-2E are partial side views of other example embodiments of an angiography catheter;

FIGS. 3A and 3B are partial side views of an example embodiment of an embolic protection device;

FIGS. 4A-4D are partial side views of another example embodiment of an embolic protection device;

FIGS. 5A and 5B show partial side views of an example embodiment of an alternative deployment mechanism for an embolic protection device;

FIG. 5C is an example embodiment of a transverse cross-sectional view of the deployment mechanism for the embolic protection device of FIGS. 5A and 5B along the line 5C-5C in FIG. 5B;

FIG. 5D shows a partial side view of the deployment mechanism for the embolic protection device of FIGS. 5A-5C;

FIG. 5E shows a partial top view of the deployment mechanism for the embolic protection device of FIGS. 5A-5D;

FIGS. 6A and 6B are partial side views of another example embodiment of an embolic protection device;

FIGS. 7A and 7B are partial side views of another example embodiment of an embolic protection device;

FIG. 7C is a bottom view of the embolic protection device of FIGS. 7A and 7B;

FIGS. 8A-8D are partial side views of another example embodiment of an embolic protection device;

FIG. 9 is a partial side view of another example embodiment of an embolic protection device;

DETAILED DESCRIPTION

Figure 2A:
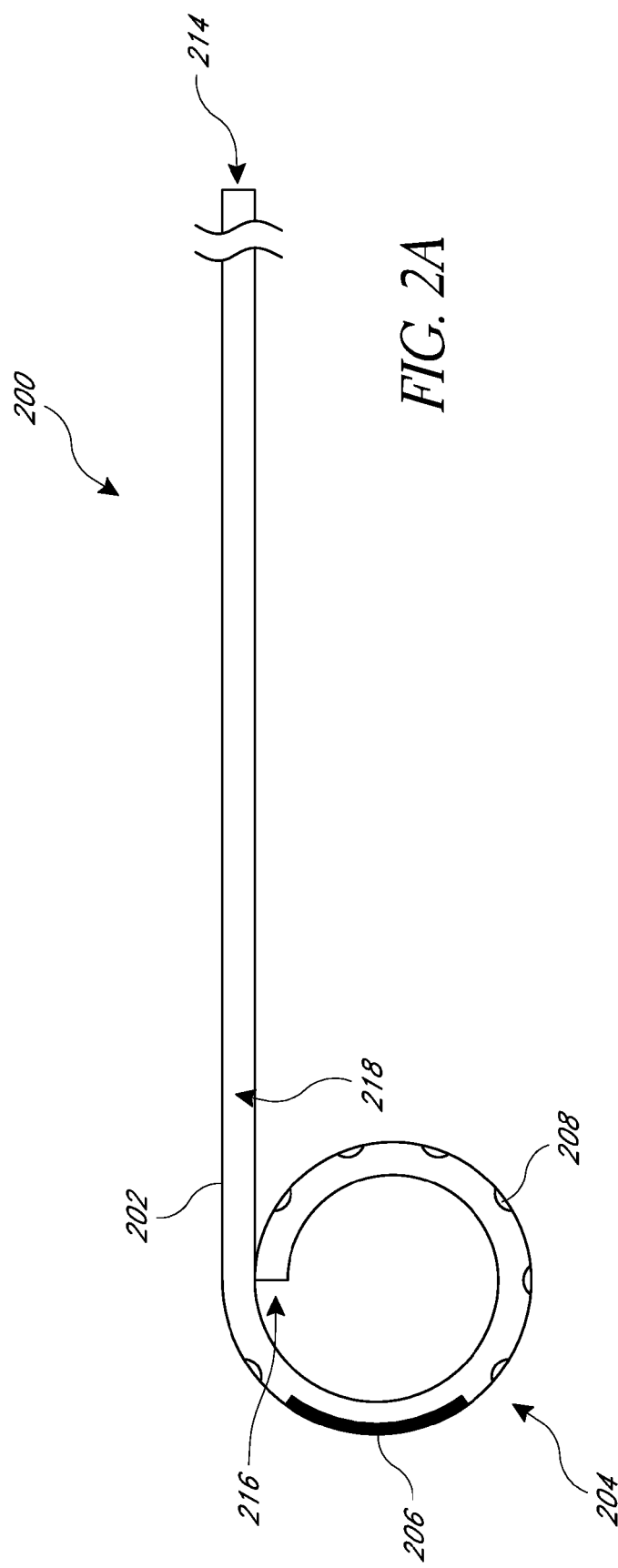
FIG. 2A is a partial side view of an example embodiment of an angiography catheter.

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

FIGS. 1A-1D illustrate example embodiments of an embolic protection device 100. The device 100 comprises a pigtail catheter 102 having a proximal end 114, distal end 116, and a lumen 118 extending from the proximal end 114 to the distal end 116. The lumen 118 is configured to house a guidewire 740 (FIGS. 7A and 7B). The pigtail catheter 102 includes a distal portion 104 configured to assume a generally arcuate shape being at least a semi-circle. A side wall of the catheter 102 includes at least one aperture 108 in the distal portion 104 configured to deliver fluids. The apertures 108 (the plural intended to include embodiments in which the distal portion includes one aperture 108) are in fluid communication with the lumen 118. The distal portion 104 of the catheter 102 includes a longitudinally-extending radiopaque marker 106 that is configured to be arcuate and on the distal-most section of the catheter 102 when the distal portion 104 is in the generally arcuate shape. The device 100 further comprises a self-expanding embolic filter 110 and an outer sheath 112. The embolic filter 110 is coupled to a side of the catheter 102 proximal to the distal portion 104. When in an expanded configuration, the embolic filter 110 has a generally conical shape extending proximally from a distal opening 140 to a closed proximal end 142. The outer sheath 112 is configured to be circumferentially around at least a portion of the catheter 102 and the embolic filter 110. The outer sheath 112 is configured to contain the embolic filter 110 in a collapsed configuration when around the embolic filter 110. The outer sheath 112 is longitudinally movable with respect to the catheter 102, and can be moved proximally to release the embolic filter 110 and moved distally to recapture the embolic filter 110 and embolic material in the embolic filter 110. The embolic filter 110 is configured to self-expand upon longitudinal proximal retraction of the outer sheath. A device according to the disclosure herein can comprise some or all of the features of the embolic protection device 100 shown in FIGS. 1A-1D, and is described herein in various combinations and subcombinations.

The pigtail catheter 102 may comprise a flexible material so as to be maneuverable within a body lumen as described herein. For example, in some embodiments, the catheter 102 comprises a polymer (e.g., polyurethane, silicone, latex, polytetrafluoroethylene (PTFE), a plastic material, etc.). In some embodiments, the catheter 102 comprises a metal-reinforced plastic (e.g., including nitinol, stainless steel, etc.). Other materials are also possible. In some embodiments, the catheter 102 does not comprise latex, which may cause allergic reactions in some patients. In some embodiments, the catheter 102 comprises braid-reinforced tubing to advantageously increase the strength of the catheter 102. In some embodiments, the catheter 102 comprises a braided catheter shaft including a layer of braided wire between two layers of catheter tubing, which may increase the strength of the catheter 102. In some embodiments, the catheter 102 does not include a braided layer, which may increase the flexibility of the catheter 102. In some embodiments, the catheter 102 comprises a lubricious coating, for example a coating having a low friction coefficient, to advantageously allow for smoother navigation through tortuous vasculature. In some embodiments, the catheter 102 coating has anti-thrombotic properties to advantageously inhibit thrombus formation. In some embodiments, the catheter 102 has a size (i.e., outside diameter) between about 6 French and about 9 French (approx. between about 2 mm and about 3 mm). Other sizes are also possible, for example depending on the size of the target body lumen of a particular patient. In some embodiments, the catheter 102 has a length between about 65 centimeters (cm) and about 135 cm. Other lengths are also possible, for example to allow for insertion of the catheter 102 in the femoral, brachial, or radial artery. The catheter 102 can be manufactured, for example, by extrusion, injection molding, or another suitable process.

The radiopaque marker 106 extends longitudinally along a section of the distal portion 104 of the catheter 102. When the distal portion 104 is in the generally arcuate shape, the radiopaque marker 106 is also generally arcuate and on a distal-most section of the catheter 102. In some embodiments, the radiopaque marker 106 has a length of about 1 cm. The radiopaque marker 106 comprises a radiopaque material, for example platinum, tantalum, tungsten, palladium, and/or iridium. Other radiopaque materials are also possible. In some embodiments, a material may be considered radiopaque, for example, if the average atomic number is greater than 24, if the density is greater than about 9.9 g/cm$^3$, etc.

The embolic filter 110 has a generally conical shape (e.g., conical, frustoconical, etc.) and is coupled (e.g., by adhering, welding, soldering, coupling using a separate component, combinations thereof, and the like) to a side of catheter 102. As shown in FIGS. 1B and 1D, the embolic filter 110 includes a distal opening 140 and extends proximally from the distal opening 140 to a closed proximal end 142. In some embodiments, the distal opening 140 of the embolic filter 110 has a diameter of about 4.5 cm. The embolic filter 110 can be made in different sizes having different diameters for patients with different sized blood vessels. In some embodiments, the shape of the distal opening 140 of the embolic filter 110 is circular, oval, elliptical, oblong, egg-shaped, combinations thereof, and the like. In some embodiments, the embolic filter 110 comprises a shape memory material, for example including nitinol, chromium cobalt, and/or alloys such as MP35N, 35NLT, Elgiloy, etc. In some embodiments, the embolic filter 110 comprises a braided mesh. In some embodiments, the embolic filter 110 comprises a porous membrane, for example a semi-permeable polyurethane membrane. In some embodiments, the embolic filter 110 is laser cut from a tube or a sheet. In some embodiments, the distal opening 140 of the embolic filter 110 is attached to a self-expanding frame, for example a nitinol frame. In some embodiments, the embolic filter 110 comprises an anti-thrombogenic coating (e.g., comprising heparin or a thrombin or platelet inhibitor) to advantageously reduce thrombogenicity. The embolic filter 110 is configured to self-expand to a radially expanded, open configuration, shown in FIGS. 1B and 1D, when not confined by, for example, an outer sheath 112.

In some embodiments, for example as illustrated in FIGS. 1A and 1B, the embolic filter 110 is coupled to the catheter 102 on the side of the catheter facing the distal portion 104 when the distal portion 104 is in the generally arcuate shape. In some embodiments, for example as illustrated in FIGS. 1C and 1D, the embolic filter 110 is coupled to the catheter 102 on the side of the catheter facing away from the distal portion 104 when the distal portion 104 is in the generally arcuate shape. The embolic filter 110 can also be coupled to any other side of the catheter 102 (e.g., orthogonal to a plane of the arcuate member). In some embodiments, the embolic filter 110 is coupled to the catheter 102 along the entire length of the embolic filter 110. In some embodiments, the embolic filter 110 is coupled to the catheter 102 at the proximal and/or distal ends of the embolic filter 110 and/or at any other points there between.

The outer sheath 112 comprises a hollow tube configured to circumferentially surround at least a portion of the catheter 102. Outer sheath 112 is longitudinally movable with respect to the catheter 102 and is configured to at least partially contain (e.g., contain) the embolic filter 110 in a collapsed configuration when circumferentially surrounding the embolic filter 110, for example, as shown in FIGS. 1A and 1C. The outer sheath 112 is longitudinally proximally retractable to release the embolic filter 110. The embolic filter 110 self-expands to the expanded, open configuration when not contained by the outer sheath 112. In some embodiments, the outer sheath 112 extends proximally to the proximal end 114 of the catheter 102 so that the user can grasp and manipulate the outer sheath 112 directly. In some embodiments, the outer sheath 112 extends proximally over only a portion of the catheter 102, and a secondary device (e.g., a push-rod such as found in stent deployment systems) is coupled to the outer sheath 112 (e.g., to the proximal end of the outer sheath 112) to allow for indirect manipulation of the outer sheath 112. Manipulation of the outer sheath 112 may be mechanical, electronic, manual, combinations thereof, and the like.

FIG. 2A illustrates an example embodiment of an angiography catheter 200. The illustrated embodiment includes a flexible pigtail-type catheter 202 having a proximal end 214, distal end 216, and a lumen 218 extending from the proximal end 214 to the distal end 216. The lumen 218 is configured to house a guidewire 740 (FIGS. 7A and 7B). The catheter 202 has a distal portion 204 configured to assume a generally arcuate shape and a radiopaque marker 206 on the distal portion 204.

The catheter 202 may comprise a flexible material so as to be maneuverable within a body lumen as described herein. For example, in some embodiments, the catheter 202 comprises a polymer (e.g., polyurethane, silicone, latex, polytetrafluoroethylene (PTFE), a plastic material, etc.). In some embodiments, the catheter 202 comprises a metal-reinforced plastic (e.g., including nitinol, stainless steel, etc.). Other materials are also possible. In some embodiments, the catheter 202 does not comprise latex, which may cause allergic reactions in some patients. In some embodiments, the catheter 202 comprises a braided catheter shaft including a layer of braided wire between two layers of catheter tubing, which may increase the strength of the catheter 202. In some embodiments, the catheter 202 does not included a braided layer, which may increase the flexibility of the catheter 202. In some embodiments, the catheter 202 comprises a lubricious coating, for example a coating having a low friction coefficient, to advantageously allow for smoother navigation through tortuous vasculature. In some embodiments, the catheter 202 coating has anti-thrombotic properties, to advantageously inhibit thrombus formation. In some embodiments, the catheter 202 has a size (i.e., outside diameter) between about 6 French and about 9 French (approx. between about 2 mm and about 3 mm). Other sizes are also possible, for example depending on the size of the target body lumen of a particular patient. In some embodiments, the catheter 202 has a length between about 65 cm and about 135 cm. Other lengths are also possible, for example to allow for insertion of the catheter 102 in the femoral, brachial, or radial artery. The catheter 202 can be manufactured, for example, by extrusion, injection molding, or another suitable process.

As shown in FIG. 2A, a distal portion 204 of the catheter 202 is configured to assume a generally arcuate shape like a pigtail catheter. When a guidewire is in the lumen 218, the guidewire substantially straightens the distal portion 204 of the catheter 202, allowing the catheter 202 to maneuver through body lumens as described herein. When the guidewire is withdrawn from at least the distal portion 204 of the catheter 202 as described herein, the distal portion 204 assumes the generally arcuate shape. In some embodiments, the generally arcuate shape is at least about a semi-circle. In some embodiments, the generally arcuate shape is at least about three-quarters of a circle. In some embodiments, the generally arcuate shape is at least about 350°. In some embodiments, the generally arcuate shape is at least about a full circle. In some embodiments, the generally arcuate shape is greater than about 90°. Non-circular arcuate shapes (e.g., oval, oblong, elliptical, egg-shaped, spiral, etc.) are also possible, and descriptions of the terms circle, diameter, and the like herein should be interpreted in view of the arcuate shape of the distal portion 204. In some embodiments, the distal portion 204 of the catheter 202 has a diameter of less than about 1 cm when the distal portion 204 is in the generally arcuate shape. In some embodiments, the diameter of the distal portion 204 is less than about 0.75 cm. In some embodiments, for example when the angiography catheter 200 is used during a valve replacement procedure, a diameter of less than about 0.75 cm for the distal portion 204 can facilitate placement of the distal portion 204 within or adjacent to a noncoronary cusp of a patient.

In some embodiments, the proximal end 214 of the catheter 202 is configured to be coupled to a contrast material injector and the lumen 218 is also configured to provide a flow path for contrast material from the proximal end 214 to the distal end 216 of the catheter 202. For example, the proximal end 214 may include a Luer or other fitting. A side wall of the catheter 202 may include at least one aperture 208 in the distal portion 204. The aperture 208 is in fluid communication with the lumen 218, so that contrast material, drugs such as anti-thrombotics, etc. injected into the lumen 218 can be dispersed from the aperture 208, and optionally an opening at the distal end 216 of the catheter 202. In some embodiments, the distal end 216 is closed, for example being configured to inwardly collapse when not held open by a guidewire. In some embodiments, the distal end 216 is partially open to allow for pressure measurements.

The embodiment of angiography catheter 200 illustrated in FIG. 2A comprises a radiopaque marker 206. The radiopaque marker 206 comprises a radiopaque material, for example platinum, tantalum, tungsten, palladium, and/or iridium. Other radiopaque materials are also possible. In some embodiments, a material may be considered radiopaque, for example, if the average atomic number is greater than 24, if the density is greater than about 9.9 g/cm$^3$, etc.

As explained herein, during certain cardiac procedures, precise placement of instruments and devices can be important. For example, when performing a percutaneous cardiac valve replacement procedure, the replacement valve device should be placed no more than about 4-6 mm below the lower border of the aortic annulus. Therefore, the user can preferably identify the lower border of the annulus to use as a reference point. The radiopaque marker 206 advantageously allows the user to define and visualize the lower border of the annulus or other anatomic landmarks. A typical pigtail catheter without a radiopaque marker can be used for visualization during a procedure through the injection of contrast material. However, a radiopaque marker or markers on the catheter itself can advantageously reduce contrast load and allow uninterrupted identification of the lower border of the aortic annulus or other anatomic landmarks.

The size and positioning of radiopaque marker 206 may provide additional benefits. For example, making the entire distal portion 204 of the catheter 202 radiopaque could result in the distal portion 204 being too stiff for maneuverability and assuming the arcuate shape. The radiopaque marker 206 illustrated in FIG. 2A extends longitudinally along the outer curvature of the distal portion 204 of the catheter 202 similar to the radiopaque marker 106 shown in FIGS. 1A-1D and described herein. When the distal portion 204 of the catheter 202 is substantially straight (e.g., due to a guidewire being in the lumen 218), the distal end 216 of the catheter 202 is the distal-most section of the catheter 202. When the distal portion 204 of the catheter 202 assumes the generally arcuate shape, the distal end 216 of the catheter 202 curves at least partially proximally, so the distal end 216 is not the distal-most section of the catheter 202. Rather, the distal-most section of the catheter 202 the section of the catheter 202 beyond which no other section of the catheter 202 is distal, which is the bottom curved section of the generally arcuate distal portion 204. The radiopaque marker 206 of FIG. 2A is configured to be on the distal-most section of the catheter 202 when the distal portion 204 is in the generally arcuate shape. This configuration may provide the unique advantage of precisely identifying the distal-most edge of the catheter 202 when the distal portion 204 is in the generally arcuate shape, thereby allowing the user to define an anatomic landmark, e.g., the lower border of the aortic annulus. In some embodiments, the radiopaque marker 206 has a length of about 1 cm. In some embodiments, the radiopaque marker 206 has a length of about 0.8 cm. In some embodiments, the radiopaque marker 206 has a length of about 0.5 cm. Other lengths of the radiopaque marker 206 are also possible.

FIGS. 2B and 2C illustrate example embodiments of a radiopaque marker 206. FIG. 2B illustrates an embodiment in which the radiopaque marker 206 is generally arcuate and configured to be on the distal-most section of the catheter 202 when the distal portion 204 is in the generally arcuate shape. In the embodiment illustrated in FIG. 2B, the radiopaque marker 206 is configured to be on the inner curvature of the distal-most section of the catheter 202 when the distal portion 204 is in the generally arcuate shape. Certain such embodiments may advantageously inhibit contact of body tissue by the radiopaque marker 206, which may be harder than the material of the catheter 202. FIG. 2C illustrates an embodiment in which the radiopaque marker 206 comprises a plurality of radiopaque markers 206 transversely at least partially (e.g., fully) encircling the catheter 202. The radiopaque markers 206 are configured to be on the distal-most section of the catheter 202 when the distal portion 204 is in the generally arcuate shape. Certain such embodiments may advantageously show a three-dimensional view of the distal-most section of the catheter 202 and/or may be visible from various perspectives. FIG. 2C shows six radiopaque markers 206; however, more or fewer radiopaque markers 206 are possible. Spacing and/or thickness of the radiopaque markers 206 may be consistent or may vary from proximal to distal, towards a center or edge of the radiopaque marker 206, etc. Configurations of radiopaque markers 206 other than those shown in FIGS. 2A-2C are also possible.

In some embodiments, for example as shown in FIG. 2A, the apertures 208 are on an outer curved wall of the distal portion 204 of the catheter 202 when the distal portion 204 is in the generally arcuate shape. Other configurations of the apertures 208 are also possible. For example, FIG. 2D illustrates an embodiment in which the apertures 208 are substantially transverse (e.g., transverse) to the plane of the distal portion 204 when the distal portion 204 is in the generally arcuate shape. The apertures 208 can be on one or both sides of the distal portion 204. For another example, FIG. 2E illustrates an embodiment in which the apertures 208 are on both the inner and outer curvature of the distal portion 204 of the catheter 202 when the distal portion 204 is in the generally arcuate shape. The apertures 208 shown in FIG. 2E alternate consecutively between the inner and outer curvature, but other arrangements are possible. Certain configurations of the apertures 208 may advantageously reduce fluid forces that would cause the distal portion 204 to straighten. In some embodiments, the apertures 208 are located in the same section of the distal portion 204 where the radiopaque marker 206 is located. In some embodiments, there are no apertures 208 in the same section of the distal portion 204 as the radiopaque marker 206.

In some embodiments, the apertures 208 are configured to counteract forces on the distal portion 204 resulting from fluid ejection from an optional opening in the distal end 216 of the catheter 202. For example, the force of fluid exiting an opening in the distal end 216 of the catheter 202 may tend to uncurl the distal portion 204 or cause the distal portion 204 to lose the generally arcuate shape. The apertures 208 can be configured so that the force of fluid exiting from the apertures 208 at least partially opposes any force tending to uncurl the distal portion 204 to aid the distal portion 204 of the catheter 202 in maintaining the generally arcuate shape.

FIGS. 3A and 3B illustrate an example embodiment of an embolic protection device 300 comprising a catheter 302, an embolic filter 310, and a movable outer sheath 312. The catheter 302 may include at least one lumen therethrough. The catheter 302 may comprise a flexible material such as a polymer (e.g., polyurethane, silicone, latex, polytetrafluoroethylene (PTFE), nylon, a plastic material, etc.) so as to be maneuverable within a body lumen as described herein. In some embodiments, the catheter 302 comprises a metal-reinforced plastic (e.g., including nitinol, stainless steel, etc.). Other materials are also possible. In some embodiments, the catheter 302 does not comprise latex, which may cause allergic reactions in some patients. In some embodiments, the catheter 302 comprises a braided catheter shaft including a layer of braided wire between two layers of catheter tubing, which may increase the strength of the catheter 302. In some embodiments, the catheter 302 does not included a braided layer, which may increase the flexibility of the catheter 302. In some embodiments, the catheter 302 comprises a lubricious coating, for example a coating having a low friction coefficient, to advantageously allow for smoother navigation through tortuous vasculature. In some embodiments, the catheter 102 coating has anti-thrombotic properties, to advantageously inhibit thrombus formation. In some embodiments, the catheter 302 has a size (i.e., outside diameter) between about 6 French and about 9 French (approx. between about 2 mm and about 3 mm). Other sizes are also possible, for example depending on the size of the target body lumen of the particular patient. In some embodiments, the catheter 302 has a length between about 65 cm and about 135 cm. Other lengths are also possible, for example to allow for insertion of the catheter 302 in the femoral, brachial, or radial artery. The catheter 302 can be manufactured, for example, by extrusion, injection molding, or another suitable process.

The embolic filter 310 has a generally conical shape (e.g., conical, frustoconical, etc.) and is coupled (e.g., by adhering, welding, soldering, coupling using a separate component, combinations thereof, and the like) to a side of catheter 302. In some embodiments, the embolic filter 310 is coupled to the catheter 302 along the entire length of the embolic filter 310. In some embodiments, the embolic filter 310 is coupled to the catheter 302 at the proximal and/or distal ends of the embolic filter 310 and/or any other points there between. As shown in FIG. 3B, the embolic filter 310 includes a distal opening 340 and extends proximally from the distal opening 340 to a closed proximal end 342. In some embodiments, the distal opening 340 of the embolic filter 310 has a diameter of about 4.5 cm. The embolic filter 310 can be made in different sizes having different diameters for patients with different sized blood vessels. In some embodiments, the shape of the distal opening 340 of the embolic filter 310 is circular, oval, elliptical, oblong, egg-shaped, combinations thereof, and the like. In some embodiments, the embolic filter 310 comprises a shape memory material, for example including nitinol, chromium cobalt, and/or alloys such as MP35N, 35NLT, Elgiloy, etc. In some embodiments, the embolic filter 310 comprises a porous membrane, for example a semi-permeable polyurethane membrane. In some embodiments, the embolic filter 310 comprises a braided mesh. In some embodiments, the embolic filter 310 is laser cut from a tube or a sheet. In some embodiments, the distal opening 340 of the embolic filter 310 is attached to a self-expanding frame, for example a nitinol frame. In some embodiments, the embolic filter 310 comprises an anti-thrombogenic coating (e.g., comprising heparin or a thrombin or platelet inhibitor) to advantageously reduce thrombogenicity. The embolic filter 310 is configured to self-expand to a radially expanded, open configuration, shown in FIG. 3B, when not confined by, for example, an outer sheath 312.

In use, the embolic filter 310 is configured to be placed in a body lumen, e.g., blood vessel, of a patient, and in the expanded, open configuration, the perimeter of the open distal end 340 engages the interior lumen wall. The embolic filter 310 is oriented so that the distal opening 340 is configured to face the upstream direction of blood flow. Because the distal end of the embolic filter 310 engages the interior lumen wall, substantially all (e.g., all) blood flow is directed into and through the embolic filter 310 rather than around the embolic filter 310. The embolic filter 310 has a pore size large enough to allow blood to pass through freely, yet small enough that embolic debris cannot pass through the embolic filter 310. For example, the pore size of the embolic filter 310 can be in the range of about 40 μm to about 200 μm, for example about 100 μm. The pore size can be uniform throughout the embolic filter 310. The pore size can vary (e.g., increase, decrease, and combinations thereof) throughout the embolic filter 310, for example from the proximal end of the embolic filter 310 to the distal end of the embolic filter 310. Embolic material or debris (e.g., particles resulting from aortic cross-clamping, dislodged plaque, thrombi, other cardiac manipulation, etc.) in the blood stream may therefore be trapped in the embolic filter 310 so that the debris does not migrate to other parts of the body and potentially cause complications. For example, during a procedure on a patient's aortic valve, the embolic filter 310 can be positioned so that the distal opening 340 is in the ascending aorta below the carotid arteries. Embolic debris dislodged during the procedure can be trapped in the embolic filter 310 before reaching the carotid arteries where the debris could travel to the brain and cause a stroke or the descending aorta where the debris could travel to other parts of the body and cause embolization to e.g., the periphery, kidneys, and/or bowel.

The outer sheath 312 comprises a hollow tube configured to circumferentially surround at least a portion of the catheter 302. Outer sheath 312 is longitudinally movable with respect to the catheter 302 and is configured to at least partially contain (e.g., contain) the embolic filter 310 in a collapsed configuration when circumferentially surrounding the embolic filter 310, for example as shown in FIG. 3A. The outer sheath 312 is longitudinally proximally retractable to release the embolic filter 310. The embolic filter 310 self-expands to the expanded, open configuration when not contained by the outer sheath 312. In some embodiments, the outer sheath 312 extends proximally to the proximal end of the catheter 302 so that the user can grasp and manipulate the outer sheath 312 directly. In some embodiments, the outer sheath 312 extends proximally over only a portion of the catheter 302, and a secondary device (e.g., a push-rod such as found in stent deployment systems) is coupled to the outer sheath 312 (e.g., to the proximal end of the outer sheath 312) to allow for indirect manipulation of the outer sheath 312. Manipulation of the outer sheath 312 may be mechanical, electronic, manual, combinations thereof, and the like.

In some embodiments, the outer sheath 312 can include an optional lip 332 protruding inwardly from the distal end of the outer sheath 312. The catheter 302 can include one or more shoulders 334 (e.g., a distal shoulder 334a and a proximal shoulder 334b) protruding outwardly from an outer wall of the catheter 302. The lip 332 of the outer sheath 312 is configured to engage the lip or lips 334 of the catheter 302 to inhibit (e.g., prevent) the outer sheath 312 from moving too far in either the proximal or distal direction. The lip 332 and shoulder 334 may be arcuate, pronged, and combinations thereof. In some embodiments, the outer sheath 312 and/or the catheter 302 comprise nubs and/or detents configured to provide information to the user about the longitudinal position of the outer sheath without inhibiting further movement. In some embodiments, the outer sheath 312 and the catheter 302 comprise lips 332, shoulders 334, and detents and nubs (e.g., to inhibit longitudinal movement of the outer sheath 312 too far in either direction, and to provide information about the extent of movement of the outer sheath 312 relative to the catheter 302 (e.g., ½ retracted, ¼ retracted, etc.)).

Benefits of the outer sheath 312 deployment mechanism may include its simplicity, ease of operation, and small number of moving parts. The embolic protection device 300 is well-suited for use in conjunction with delicate cardiac procedures having serious risks. As the duration of the procedure increases, the risk of complications typically increases as well. Therefore, it can be advantageous that the user be able to quickly and easily deploy and recapture the embolic filter 310. A more complicated device could be more difficult to operate and could be more likely to malfunction or cause adverse effects. The ability to move the outer sheath 312 relative to the filter 310 can advantageously allow the user to partially recapture the embolic filter 310, for example to adjust the width of the distal opening 340. In some embodiments, narrowing the distal opening 340 allows the user to introduce a second catheter or instrument to the patient's body lumen and maneuver the second catheter or instrument around and past the catheter 302 and embolic filter 310, as described herein.

FIGS. 4A-4D illustrate an example embodiment of an embolic protection device 400 in which the embolic filter 410 is movably coupled to the catheter 402 and is longitudinally movable with respect to the catheter 402. In some embodiments, the embolic filter 410 is coupled to an intermediate tube 430 that at least partially circumferentially (e.g., circumferentially) surrounds the catheter 402. The intermediate tube 430 is longitudinally movable with respect to the catheter 402. The outer sheath 412 is configured to at least partially circumferentially (e.g., circumferentially) surround both the catheter 402 and the intermediate tube 430. The intermediate tube 430 and the outer sheath 412 can be moved simultaneously and independently. The longitudinal position of the embolic filter 410 with respect to the catheter 402 can be adjusted while the embolic filter 410 is in the collapsed configuration or in a deployed or partially deployed, expanded configuration. In some embodiments, the perimeter of the distal opening of the embolic filter 410 comprises one or more radiopaque markers to allow the user to visualize the position of the distal opening, for example, with respect to various anatomical landmarks. For example, if the user is performing a procedure on a patient's aortic valve and wants to prevent emboli from entering the carotid arteries, the radiopaque markers can be used to ensure the distal opening of the embolic filter 410 is positioned in the ascending aorta upstream from the carotid arteries.

FIG. 4A shows the embolic filter 410 confined in a closed configuration by the outer sheath 412 and a distal end of intermediate tube 430 at position a. If the intermediate tube 430 is held stationary at position a, the outer sheath 412 can be retracted to deploy the embolic filter 410, as shown in FIG. 4C. If the intermediate tube 430 and outer sheath 412 are instead moved simultaneously, the embolic filter 410 remains confined by the outer sheath 412 while the longitudinal position of the embolic filter 410 is adjusted. For example, FIG. 4B shows the embolic filter 410 still confined by outer sheath 412, but the intermediate tube 430 has been retracted so that the distal end of the intermediate tube 430 is at position b. If the intermediate tube 430 is then held stationary at position b, the outer sheath 412 can be retracted to deploy the embolic filter 410, as shown in FIG. 4D. The intermediate tube 430 and outer sheath 412 can be moved to adjust the longitudinal position of the embolic filter 410 in a deployed or partially deployed configuration. For example, the intermediate tube 430 and outer sheath 412 can be moved simultaneously to retract the intermediate tube 430 from the position a as shown in FIG. 4C to the position b as shown in FIG. 4D. When the embolic filter 410 is partially deployed, the embolic filter 410 may not be in contact with the vessel walls and freely movable, for example due to lack of wall apposition. When the embolic filter 410 is fully deployed, any debris dislodged during movement may be trapped in the embolic filter 410.

FIGS. 5A and 5B illustrate an example embodiment of an embolic protection device 500 comprising a deployment mechanism including a movable four-pillar outer cover 512. FIG. 5C illustrates a cross-sectional view of the catheter 502 and outer cover 512 of FIGS. 5A and 5B taken along the line 5C-5C in FIG. 5B. Like the outer sheath 112 shown in FIGS. 1A-1D, the outer cover 512 is configured to circumferentially surround at least a portion of the catheter 502. Outer cover 512 is longitudinally movable with respect to the catheter 502 and is configured to at least partially contain (e.g., contain) the embolic filter 510 in a collapsed configuration when circumferentially surrounding the embolic filter 510, for example, as shown in FIG. 5A. The outer cover 512 is longitudinally proximally retractable to release the embolic filter 510, as shown in FIG. 5B.

As shown in FIGS. 5A-5C, two pillars 550a can be on the same side of the catheter 502 as the embolic filter 510. The other two pillars 550b can be on the opposite side of the catheter 502 from the embolic filter 510. In some embodiments, the two filter side pillars 550a can be coupled by a connector 554 so that pillars 550a move in unison. The two non-filter side pillars 550b can also be coupled by a connector 554 to move in unison. In some embodiments, the connectors 554 have a longitudinal length at least about the longitudinal length of the embolic filter 510 when the embolic filter 510 is in the collapsed state. In some embodiments, stabilizers 552 span the distances between adjacent filter side pillars 550a and non-filter side pillars 550b, as shown in FIG. 5C. The stabilizers 552 can be solid or fenestrated. In some embodiments, the stabilizers 552 have a longitudinal length at least about the longitudinal length of the embolic filter 510 when the embolic filter 510 is in the collapsed state. In some embodiments, the stabilizers 552 are fixed with respect to the non-filter side pillars 550b. In some embodiments, the filter side pillars 550a have longitudinal grooves configured to receive and act as a track for the stabilizers 552, and the stabilizers 552 are configured to slide within the grooves.

In some embodiments, the outer cover 512 comprises a removable clip 560, shown in FIGS. 5A and 5B. The clip 560 is configured to be attached to the proximal ends of the pillars 550a, 550b. When the clip 560 is attached, the filter side pillars 550a move in unison with the non-filter side pillars 550b so that all four pillars can be moved together, for example to fully deploy the embolic filter 510, for example as shown in FIG. 5B, and/or to recapture the embolic filter 510. When the clip 560 is not attached, the filter side pillars 550a can be moved independently of the non-filter side pillars 550b. For example, if all four pillars 550a, 550b have been retracted to fully deploy the embolic filter 510, the non-filter side pillars 550b can be held in place while the filter side pillars 550a are advanced, for example as shown in FIGS. 5D and 5E, so that the connector 554 between the filter side pillars 550a covers part of the embolic filter 510. If the stabilizers 552 are fixed with respect to the non-filter side pillars 550b, the stabilizers 552 also remain in place and the grooves of the filter side pillars 550a allow the filter side pillars 550a to slide along the stabilizers 552.

The ability to independently move the filter side pillars 550a and non-filter side pillars 550b can advantageously allow the user to partially recapture the embolic filter 510, for example to adjust the width of the distal opening 540. In some embodiments, narrowing the distal opening 540 allows the user to introduce a second catheter or instrument to the patient's body lumen and maneuver the second catheter or instrument around and past the catheter 502 and embolic filter 510, as described herein. The connector 554 between the filter side pillars 550a can also serve as a deflection surface for the second catheter or instrument to assist the user in guiding the catheter or instrument past the embolic filter 510 to the desired location. In some embodiments, the four pillar outer cover 512 can advantageously allow blood to flow through the body lumen more freely compared to a solid outer sheath, which may allow blood to become trapped between the catheter and outer sheath.

In addition to those described in detail herein, a wide variety of deployment mechanisms for embolic filters are possible. For example, a deployment system may comprise a portion of an annular sheath including inward end protrusions that are guided in tracks along the catheter body. Certain such embodiments may advantageously reduce the profile of the catheter. For another example, a deployment system may comprise a threaded sheath that longitudinally moves upon twisting by the user. For yet another example, a deployment system may comprise a plurality of annular bands that can capture the embolic filter longitudinally and/or circumferentially. Combinations of the deployment systems described herein and other deployment systems are also possible.

FIGS. 6A and 6B illustrate another example embodiment of an embolic protection device 600. In the embodiment illustrated in FIGS. 6A and 6B, the embolic filter 610 is disposed around the catheter 602 rather than being coupled to a side of the catheter 602. In some embodiments, this configuration advantageously allows the distal opening 640 of the embolic filter 610 to more completely engage the interior body lumen wall. For example, when an embolic filter is attached to a side of a catheter, for example as shown in FIGS. 3A and 3B, the catheter may be between the embolic filter and the interior body lumen wall where the embolic filter is attached to the catheter. However, a side attachment can advantageously allow for the user to better maneuver other instruments around the catheter and filter.

The embolic protection device 600 comprises an outer sheath 612 deployment mechanism similar to that of embolic protection device 300 illustrated in FIGS. 3A and 3B, although other deployment mechanisms are also possible (e.g., similar to the deployment mechanism illustrated in FIGS. 5A-5E). The four-pillar outer cover 512 deployment mechanism illustrated in FIGS. 5A-5E can provide additional benefits when used with the embolic protection device 600. For example, the ability to move the filter side pillars 550a and non-filter side pillars 550b independently can advantageously allow the user to selectively deploy and/or recapture one side of the embolic filter 610, for example to allow other instruments to pass by that side of the catheter 602 and the filter 610, but to continue to capture debris in the portion that remains deployed. In some embodiments, the open distal end 640 of the embolic filter 612 is not radially fixed with respect to the catheter 602. For example, the distal end 640 embolic filter 610 may not be coupled to the catheter 602 so that movement of the catheter 602 causes relatively less movement of the distal end 640 of the embolic filter 610. Therefore, the open distal end 640 can maintain contact with the interior body lumen wall even if the catheter 602 shifts radially within the body lumen. In some embodiments, the embolic filter 610 is coupled to an intermediate tube that at least partially circumferentially surrounds the catheter 602, for example similar to the configuration described with respect to FIGS. 4A-4D.

FIGS. 7A-7C illustrate another example embodiment of an embolic protection device 700. Certain aspects of the embolic protection device 700 are similar to the embolic protection device 100 illustrated in FIGS. 1A-1D and described herein. The device 700 comprises a flexible pigtail catheter 702 having a proximal end 714, distal end 716, and a lumen 718 extending from the proximal end 714 to the distal end 716. The lumen 718 is configured to house a guidewire. The catheter 702 has a distal portion 704 configured to assume a generally arcuate shape and a radiopaque marker 706 on the distal portion 704. The device 700 further comprises a deflector 760 rather than an embolic filter 110.

The catheter 702 can be similar to the catheter 202 shown in FIGS. 2A-2E and can have any or all of the features and/or benefits shown and described with respect to catheter 202. For example, the catheter 702 may comprise a flexible material so as to be maneuverable within a body lumen as described herein. For example, in some embodiments, the catheter 702 comprises a polymer (e.g., polyurethane, silicone, latex, polytetrafluoroethylene (PTFE), a plastic material, etc.). In some embodiments, the catheter 702 comprises a metal-reinforced plastic (e.g., including nitinol, stainless steel, etc.). Other materials are also possible. In some embodiments, the catheter 702 does not comprise latex, which may cause allergic reactions in some patients. In some embodiments, the catheter 702 comprises a braided catheter shaft including a layer of braided wire between two layers of catheter tubing, which may increase the strength of the catheter 702. In some embodiments, the catheter 702 does not include a braided layer, which may increase the flexibility of the catheter 702. In some embodiments, the catheter 702 comprises a lubricious coating, for example a coating having a low friction coefficient, to advantageously allow for smoother navigation through tortuous vasculature. In some embodiments, the catheter 702 coating has anti-thrombotic properties, to advantageously inhibit thrombus formation. In some embodiments, the catheter 702 has a size (i.e., outside diameter) between about 6 French and about 9 French (approx. between about 2 mm and about 3 mm). Other sizes are also possible, for example depending on the size of the target body lumen of a particular patient. In some embodiments, the catheter 702 has a length between about 65 cm and about 135 cm. Other lengths are also possible, for example to allow for insertion of the catheter 702 in the femoral, brachial, or radial artery. The catheter 702 can be manufactured, for example, by extrusion, injection molding, or another suitable process.

A distal portion 704 of the catheter 702 is configured to assume a generally arcuate shape like a pigtail catheter. When a guidewire is in the lumen 718, the guidewire substantially straightens the distal portion 704 of the catheter 702, allowing the catheter 702 to maneuver through body lumens as described herein. When the guidewire is withdrawn from at least the distal portion 704 of the catheter 702 as described herein, the distal portion 704 assumes the generally arcuate shape. In some embodiments, the generally arcuate shape is at least about a semi-circle. In some embodiments, the generally arcuate shape is at least about three-quarters of a circle. In some embodiments, the generally arcuate shape is at least about 350°. In some embodiments, the generally arcuate shape is at least about a full circle. In some embodiments, the generally arcuate shape is greater than about 90°. Non-circular arcuate shapes (e.g., oval, oblong, elliptical, egg-shaped, spiral, etc.) are also possible, and descriptions of the terms circle, diameter, and the like herein should be interpreted in view of the arcuate shape of the distal portion 704. In some embodiments, the distal portion 704 of the catheter 702 has a diameter of less than about 1 cm when the distal portion 704 is in the generally arcuate shape. In some embodiments, the diameter of the distal portion 704 is less than about 0.75 cm. In some embodiments, for example when the device 700 is used during a valve replacement procedure, a diameter of less than about 0.75 cm for the distal portion 704 can facilitate placement of the distal portion 704 within or adjacent to a noncoronary cusp of a patient.

In some embodiments, the proximal end 714 of the catheter 702 is configured to be coupled to a contrast material injector and the lumen 718 is also configured to provide a flow path for contrast material from the proximal end 714 to the distal end 716 of the catheter 702. For example, the proximal end 714 may include a Luer or other fitting. A side wall of the catheter 702 may include at least one aperture 708 in the distal portion 704. The aperture 708 is in fluid communication with the lumen 718, so that contrast material, drugs such as anti-thrombotics, etc. injected into the lumen 718 can be dispersed from the aperture 708, and optionally an opening at the distal end 716 of the catheter 702. In some embodiments, the distal end 716 is closed, for example being configured to inwardly collapse when not held open by a guidewire. In some embodiments, the distal end 716 is partially open to allow for pressure measurements.

The distal portion of the device 700 also comprises a radiopaque marker 706. The radiopaque marker 706 comprises a radiopaque material, for example platinum, tantalum, tungsten, palladium, and/or iridium. Other radiopaque materials are also possible. In some embodiments, a material may be considered radiopaque, for example, if the average atomic number is greater than 24, if the density is greater than about 9.9 g/cm$^3$, etc. The radiopaque marker 706 can be similar to the marker of any of the example embodiments shown in FIGS. 2A-2C and described herein. For example, the radiopaque marker 706 can be a longitudinal band extending along the outer or inner curvature of the distal-most section of the catheter 702 when the distal portion 704 is in the generally arcuate shape. The radiopaque marker 706 can comprise a plurality of radiopaque markers 706 at least partially transversely encircling the catheter 702. Other configurations of radiopaque markers 706 are also possible.

In embodiments having apertures 708 in the side wall of the catheter 702 in fluid communication with the lumen 718, the apertures 708 can be similar to those of any of the example embodiments shown in FIGS. 2A and 2D-2E and described herein. For example, the apertures 708 can be on an outer curved wall of the distal portion 704 of the catheter 702 when the distal portion 704 is in the generally arcuate shape, on an inner curved wall of the distal portion 704 when the distal portion is in the generally arcuate shape, substantially transverse to the plane of the distal portion 704 when the distal portion 704 is in the generally arcuate shape, and/or some combination thereof. Other configurations of apertures 708 are also possible.

Various types and designs of deflectors can be used with an embolic protection device such as device 700. Such deflectors can have different shapes and/or sizes and can vary in where and how they are coupled to the catheter. For example, deflectors can be made in various sizes, for example to accommodate differences in patient anatomy. In some embodiments, the deflector comprises a shape memory material, for example including nitinol, chromium cobalt, and/or alloys such as MP35N, 35NLT, Elgiloy, etc. In some embodiments, the deflector comprises a porous membrane, for example a semi-permeable polyurethane membrane, mounted to a self-expanding frame, for example a frame comprising a shape memory material.

The example deflector 760 shown in FIGS. 7A-7C has a generally butterfly or elliptical shape with two wings or petals 760a, 760b extending to either side of a central axis 764. The wings 760a, 760b may be the same or different in size shape, material, etc. The deflector 760 is coupled to a side of the catheter 702 via an elongate member 762 that is coupled (e.g., by adhering, welding, soldering, coupling using a separate component, combinations thereof, and the like) at one end to the central axis 764 of the deflector 760 and at the other end to the catheter 702. In some embodiments, the elongate member 762 comprises a shape memory material, for example including nitinol, chromium cobalt, and/or alloys such as MP35N, 35NLT, Elgiloy, etc., that is configured (e.g., shape set) to bias the deflector away from the catheter 702. The deflector 760 is configured to release to an open configuration, shown in FIGS. 7B and 7C, when not confined by, for example, an outer sheath 712. In some embodiments, the deflector 760 is configured to fold along the central axis 764 away from the elongate member 762 so that the wings or petals 760a, 760b come together and the deflector 760 can be contained in, for example, an outer sheath 712, as shown in FIG. 7A. As shown in FIG. 7A, the deflector 760 can initially be folded and contained in the outer sheath 712 such that the wings or petals 760a, 760b are positioned distal to the central axis 764. In some embodiments, the deflector 760 can initially be folded in the opposite direction such that the wings or petals 760a, 760b are positioned proximal to the central axis 764.

FIGS. 8A-8D show another example embodiment of an embolic protection device 800 having a deflector. Device 800 is similar to device 700 shown in FIGS. 7A-7C and described herein with the exception of the design of the deflector 860. Deflector 860 has a generally convex shape, for example like a somewhat flattened umbrella, parachute, or mushroom cap. In some embodiments, a frame can extend along a perimeter of the deflector 860. In some embodiments, one or more frame struts also, or alternatively, extend parallel to longitudinal or transverse axes of the deflector 860, for example to create and/or maintain the expanded shape.

The deflector 860 is coupled to a side of the catheter 802 via an elongate member 862. In some embodiments, the elongate member 862 comprises a shape memory material, for example including nitinol, chromium cobalt, and/or alloys such as MP35N, 35NLT, Elgiloy, etc., that is configured (e.g., shape set) to bias the deflector away from the catheter 802. In some embodiments, the elongate member 862 includes a plurality of arms (e.g., two arms 862a, 862b) that extend from the main body of the elongate member 862, which is coupled (e.g., by adhering, welding, soldering, coupling using a separate component, combinations thereof, and the like) to the catheter 802. In some embodiments, the elongate member includes a plurality of arms that are coupled (e.g., by adhering, welding, soldering, coupling using a separate component, combinations thereof, and the like) to the catheter. In some embodiments, the arms 862a, 862b or a plurality of elongate members 862 are coupled (e.g., by adhering, welding, soldering, coupling using a separate component, combinations thereof, and the like) to different sides of the perimeter of the deflector 860, for example as shown in FIGS. 8A-8C. In some embodiments, the arms 862a, 862b or a plurality of elongate members 862 are coupled to a portion of the deflector 860 other than the perimeter, for example as shown in FIG. 8D. In some embodiments, the arms 862a, 862b or a plurality of elongate members 862 are coupled to the deflector 860 proximate to a proximal end of the deflector 860, for example as shown in FIGS. 8A-8D. This configuration can advantageously allow the deflector 860 to more easily be recaptured by the outer sheath 812 as described herein. In certain such embodiments, during retraction of the deflector 860 back into the outer sheath 812, the distal end of the deflector may continue to deflect debris away from the branch arteries. In some embodiments, the arms 862a, 862b or a plurality of elongate members 862 are coupled to the deflector 860 proximate to a distal end of the deflector 860. In some embodiments, the arms 862a, 862b or a plurality of elongate members 862 are coupled to the deflector 860 proximate to a middle or central portion of the deflector 860. If the deflector 860 comprises a frame, the arms 862a, 862b or a plurality of elongate members 862 can be coupled to the frame.

The deflectors 760 and 860 shown in FIGS. 7A-8D and described herein are example deflectors, and other designs and configurations are possible. For example, the deflector can have a generally flat, convex, or concave shape. The deflector can be coupled to the catheter via an elongate member, such as the elongate member 762 shown in FIGS. 7A and 7B, an elongate member including multiple arms, such as the elongate member 862 shown in FIGS. 8A-8D, multiple elongate members, combinations thereof, and the like. Multiple arms can advantageously allow for better deployment from and retraction by a deployment mechanism as described herein. Fewer arms or a single arm may result in less obstruction to blood flow in use and/or may make the device less expensive to manufacture. The elongate member or members can also be coupled to the deflector at various locations. For example, an elongate member can be coupled to the center of the deflector so that the deflector is folded in the restrained configuration, for example like deflector 760 shown in FIGS. 7A and 7B. For another example, an elongate member or members can be coupled to the deflector proximate to the proximal end of the deflector, for example like deflector 860 shown in FIGS. 8A-8D, or proximate to the distal end of the deflector.

The deflectors 760 and 860 are configured to be contained, released, and recaptured by an outer sheath 712, 812 deployment mechanism. In some embodiments, the outer sheath 712, 812 is similar to outer sheath 112, 312, 412 shown in FIGS. 1A-1D, 3A-3B, and 4A-4D and described herein. The outer sheath 712, 812 comprises a hollow tube configured to circumferentially surround at least a portion of the catheter 702, 802. Outer sheath 712, 812 is longitudinally movable with respect to the catheter 702, 802 and is configured to at least partially contain (e.g., contain) the deflector 760, 860 in a collapsed configuration when circumferentially surrounding the deflector 760, 860, for example as shown in FIGS. 7A and 8A. The outer sheath 712, 812 is longitudinally proximally retractable to release the deflector 760, 860. The deflector 760, 860 unfolds and the elongate member(s) 762, 862 extends from the catheter 702, 802 to the deployed configuration when not contained by the outer sheath 712, 812, for example as shown in FIGS. 7B and 8B-8D.

In some embodiments, the outer sheath 712, 812 extends proximally to the proximal end of the catheter 702, 802 so that the user can grasp and manipulate the outer sheath 712, 812 directly. In some embodiments, the outer sheath 712, 812 extends proximally over only a portion of the catheter 702, 802, and a secondary device (e.g., a push-rod such as found in stent deployment systems) is coupled to the outer sheath 712, 812 (e.g., to the proximal end of the outer sheath 712, 812) to allow for indirect manipulation of the outer sheath 712, 812. Manipulation of the outer sheath 712, 812 may be mechanical, electronic, manual, combinations thereof, and the like. In some embodiments, the catheter 702, 802 and the outer sheath 712, 812 can include lips, shoulders, nubs, and/or detents, for example similar to those shown in FIGS. 3A and 3B and described herein. In some embodiments, the deflector 760, 860 can be movably coupled to the catheter 702, 802 and longitudinally movable with respect to the catheter 702, 802 via coupling to an intermediate tube, for example as shown in FIGS. 4A-4D and described herein. In some embodiments, the deflector 760, 860 can comprise one or more radiopaque markers, for example on the proximal and distal ends of the deflector 760, 860, to allow the user to visualize the position of the deflector 760, 860, for example, with respect to various anatomical landmarks. For example, if the user is performing a procedure on a patient's aortic valve and wants to prevent emboli from entering the carotid arteries, the radiopaque markers can be used to ensure the deflector 760, 860 is positioned so that it covers the openings to the carotid arteries. In some embodiments, the device 700, 800 can comprise an alternative four-pillar outer cover deployment mechanism, for example similar to that shown in FIGS. 5A-5E and described herein.

Although example embolic protection devices 700 and 800 comprise pigtail-type catheters, deflectors can also be coupled to other types of catheters, such as catheters that do not have distal portions configured to assume a generally arcuate shape. In some embodiments, deflectors, for example the deflectors 760 and 860, can be coupled to the side of a straight catheter.

In use, the deflector 760, 860 is configured to be placed in a primary body lumen, e.g., blood vessel, of a patient, and in the expanded, open configuration, the deflector 760, 860 spans the opening(s) of a secondary body lumen or lumens branching off from the primary body lumen. For example, the deflector 760, 860 can be placed in the aorta to cover the openings of the arteries that branch off from the aortic arch, e.g., the brachiocephalic and left common carotid arteries. Therefore, substantially all (e.g., all) blood flow to the branch arteries is directed through the deflector 760, 860. The deflector 760, 860 has a pore size large enough to allow blood to pass through freely, yet small enough that embolic debris cannot pass through the deflector 760, 860. For example, the pore size of the deflector 760, 860 can be in the range of about 40 μm to about 200 μm, for example about 100 μm. The pore size can be uniform throughout the deflector 760, 860. The pore size can vary (e.g., increase, decrease, and combinations thereof) throughout the deflector 760, 860. Embolic material or debris (e.g., particles resulting from aortic cross-clamping, dislodged plaque, thrombi, other cardiac manipulation, etc.) in the blood stream to the branch arteries may therefore be trapped in or deflected by the deflector 760, 860 so that the debris does not travel to the brain and potentially cause complications.

FIG. 9 shows another example embodiment of an embolic protection device 900 comprising a catheter 902, a deflector 960, an embolic filter 910, and a movable outer sheath 912. In some embodiments, the device 900 is similar to embolic protection device 700 with the addition of the embolic filter 910. In some embodiments, the catheter 902 is a pigtail-type catheter as shown in FIG. 9 and described herein. In some embodiments, the deflector 960 and embolic filter 910 can be coupled to another type of catheter, for example a catheter without a distal portion configured to assume an arcuate shape. The embolic filter 910 can be similar to the embolic filters 110, 310 shown in FIGS. 1A-1D and 3A-3B and described herein. In some embodiments, the embolic filter 910 is coupled to the catheter 902 proximal to the deflector 960, for example as shown in FIG. 9. In some embodiments, the embolic filter 910 is coupled to the catheter 902 distal to the deflector 960. In some embodiments, the embolic filter 910 is coupled to the same side of the catheter 902 as the deflector 960, for example as shown in FIG. 9. In some embodiments, the embolic filter 910 is coupled to a different side of the catheter 902 than the deflector 960.

The combination of the deflector 960 and the embolic filter 910 can advantageously provide additional protection against potential complications resulting from thrombi in the blood stream. For example, if the embolic filter 910 (e.g., the distal end of the embolic filter 910) is distal to the deflector 960, the embolic filter 910 can serve as the primary means of embolic protection and the deflector 960 can serve as the secondary means of embolic protection. If some blood is able to flow around the filter 910 rather than through it, the deflector 960 serves as a back-up protection device and prevents any debris not captured by the filter 910 from entering the carotid arteries and traveling to the brain. If the embolic filter 910 is proximal to the deflector 960, the deflector 960 can serve as the primary means of embolic protection and the embolic filter 910 can serve as the secondary means of embolic protection. The deflector 960 first deflects debris away from the carotid arteries, then the embolic filter 910 captures debris (e.g., including deflected debris) as blood flows through the descending aorta.

In some embodiments, the catheter 902 and outer sheath 912 can have lips, shoulders, nubs, and/or detents, for example similar to those shown in FIGS. 3A-3B and described herein. For example, lips, shoulders, nubs, and/or detents can be positioned on the catheter 902 distal to the deflector 960, between the deflector 960 and embolic filter 910, and proximal to the embolic filter 910 to engage corresponding lips, shoulders, nubs, and/or detents on the outer sheath 912. The lips, shoulders, nubs, and/or detents can advantageously provide the user with information about the longitudinal position of the outer sheath 912 so that the user knows when neither, one, or both of the deflector 960 and embolic filter 910 are deployed. In some embodiments, either or both of the deflector 960 and embolic filter 910 can be movably coupled to the catheter 902 via an intermediate tube similar to that shown in FIGS. 4A-4D and described herein. In some embodiments, the device 900 can comprise an alternative four-pillar outer cover deployment mechanism, for example similar to that shown in FIGS. 5A-5E and described herein.

In some embodiments, the embolic filter 910 can be disposed around the catheter 902 rather than coupled to a side of the catheter 902, for example similar to the embolic filter 610 of the device 600 shown in FIGS. 6A and 6B and described herein. In some embodiments, this configuration advantageously allows the embolic filter 910 to better engage the interior body lumen wall, as the position of the catheter 902 within the body lumen may be affected by the deployed deflector 860.

As described herein, FIGS. 1A and 1B illustrate an example embodiment of an embolic protection device 100 comprising a combination of features of the angiography catheter 200 illustrated in FIG. 2A and the embolic protection device 300 illustrated in FIGS. 3A and 3B. Other combinations and subcombinations of features illustrated in FIGS. 2A-6B and described herein are possible and are to be considered within the scope of this disclosure. In some embodiments, the distal portion 104 of the catheter 102 of the embolic protection device 100 can comprise any of the configurations of apertures 208 and radiopaque markers 206 shown in FIGS. 2A-2E. In some embodiments, the embolic protection device 100 can comprise the moveable embolic filter 410 illustrated in FIGS. 4A-4D and/or the alternative deployment mechanism shown in FIGS. 5A and 5B. In some embodiments, the embolic filter 110 may be disposed around the catheter 102 like the embolic filter 610 illustrated in FIGS. 6A and 6B rather than being coupled to a side of the catheter 102. in some embodiments, the outer sheath 112 and the catheter 102 of the embolic protection device 100 can have lips 332 and shoulders 334, for example as shown in FIGS. 3A and 3B, and/or detents and nubs to inhibit longitudinal movement of the outer sheath 112 relative to the catheter 102 and/or to provide information about the extent of movement of the outer sheath 112 relative to the catheter 102. In some embodiments, the catheters 302, 402, 502, and/or 602 of the embolic protection devices 300, 400, 500, and/or 600 can include a distal portion configured to assume a generally arcuate shape similar to catheter 102 illustrated in FIGS. 1A-1D and/or the catheters 202 illustrated in FIGS. 2A-2E. In some embodiments, the embolic filters 310, 410, and/or 510 of embolic protection devices 300, 400, and/or 500 can be disposed around the catheters 302, 402, and/or 502, like the embolic filter 610 illustrated in FIGS. 6A and 6B rather than being coupled to a side of the catheters 302, 402, 502. In some embodiments, the embolic protection devices 100, 300, 400, and/or 600 can comprise the deployment mechanism illustrated in FIGS. 5A and 5B. In some embodiments, embolic protection devices 100, 300, 500, and/or 600 can be coupled to the catheters 102, 302, 502, and/or 602, via an intermediate tube like the intermediate tube 430 illustrated in FIGS. 4A-4D and the embolic filters 110, 310, 510, and/or 610 can be longitudinally moveable with respect to the catheters 102, 302, 502, and/or 602. The outer sheaths 112, 412, 512, and/or 612 and the catheters 402, 502, and/or 602 of the embolic protection devices 100, 400, 500, and/or 600 can have lips 332 and shoulders 334, for example as shown in FIGS. 3A and 3B, and/or detents and nubs to inhibit longitudinal movement of the outer sheath 412, 512, and/or 612 relative to the catheter 402, 502, and/or 602 and/or to provide information about the extent of movement of the outer sheath 412, 512, and/or 612 relative to the catheter 402, 502, and/or 602. Other combinations and subcombinations of the features described herein, even if not explicitly described, are also possible.

Methods of Capturing Embolic Debris

Figure 10A:
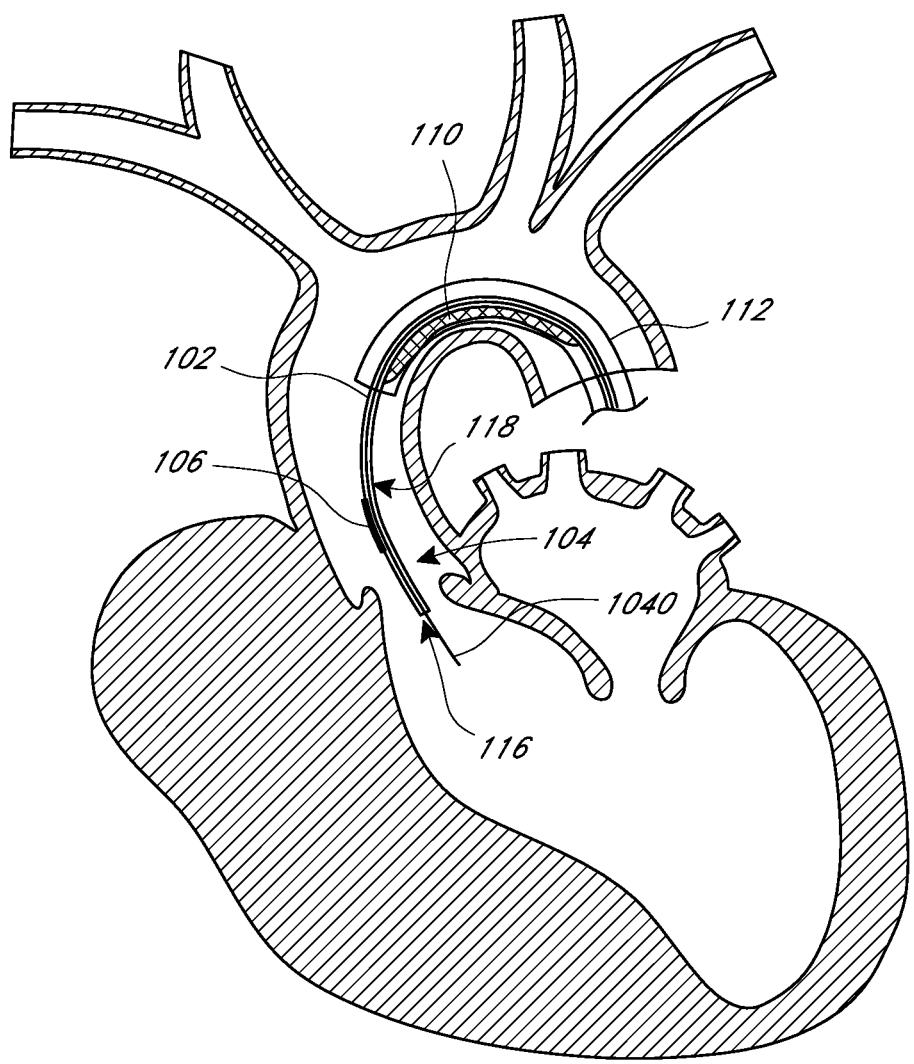
FIGS. 10A-10D show an example embodiment of a method of capturing embolic debris using an embolic protection device.
Figure 10B:
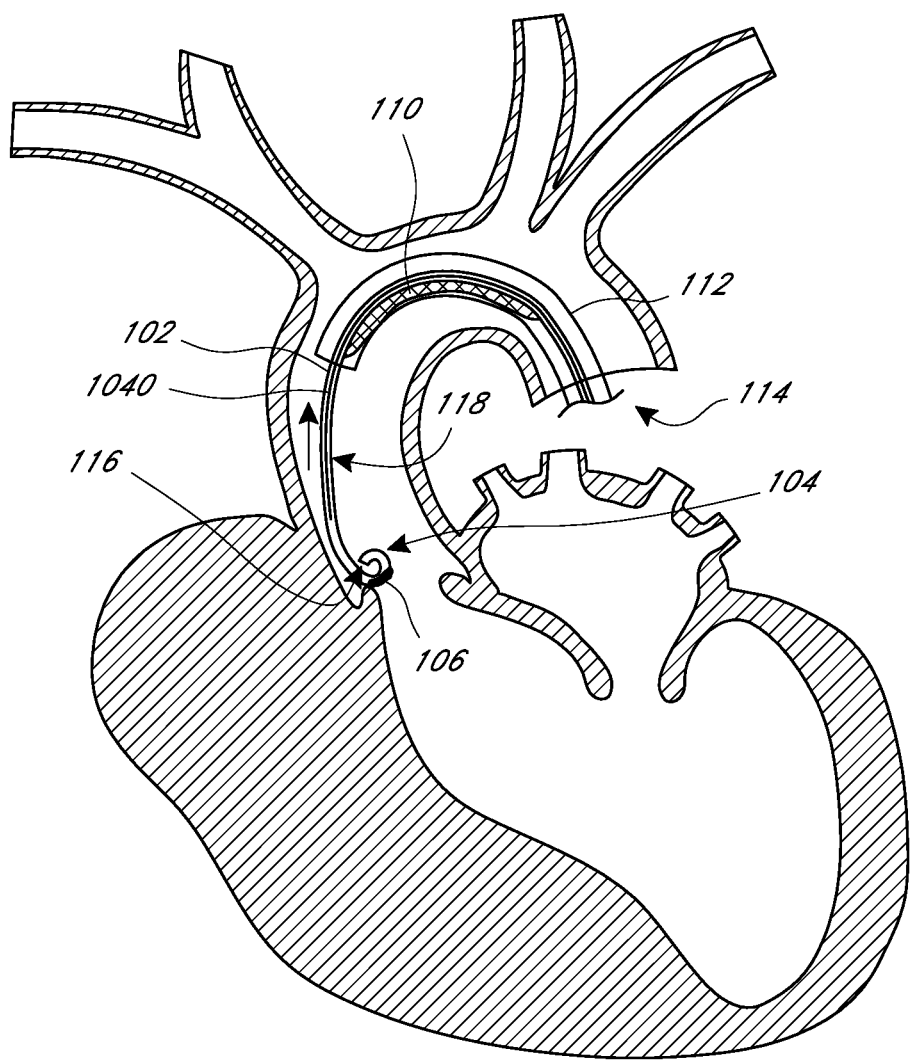

FIGS. 10A-10D show an example embodiment of a method of capturing embolic debris during a medical procedure, for example an aortic valve replacement procedure. The method can be performed using an embolic protection device 100 as described herein. According to some embodiments of the method, a guidewire 740 is percutaneously inserted into a body lumen of a patient, for example a femoral artery, a radial artery, or a brachial artery, and navigated to the desired anatomical location, for example, the level of the ascending aorta. The guidewire 740 can be a J tipped wire having a diameter of about 0.035 in. (approx. 0.089 cm). Other types and dimensions of guidewires 740 are also possible. The proximal end of the guidewire 740 is inserted into the opening at the distal end 116 of the catheter 102. When the guidewire 740 is in the lumen 118 of the catheter 102 at the distal portion 104 of the catheter 102, the distal portion 104 of the catheter is straightened or takes the curvature of the guidewire 740. The distal end 116 of the catheter 102 is inserted into the body lumen by tracking the lumen 118 of the catheter 102 over the guidewire 740, as shown in FIG. 10A. The outer diameter of the guidewire 740 is smaller than the inner diameter of the embolic protection device 100 such that the embolic protection device 100 may be tracked over the guidewire 740. The inner surface of the lumen 118 and/or the outer surface of the guidewire 740 may include a lubricious coating to reduce friction during tracking. The guidewire 740 keeps the distal portion 104 of the catheter 102 substantially straight (e.g., from being in the generally arcuate state) as the catheter 102 is inserted into and navigated within the patient's body. The radiopaque marker 106 is used to visualize and position the distal portion 104 of the catheter 102 during tracking. The guidewire 740 is removed or proximally retracted a sufficient distance to allow the distal portion 104 of the catheter 102 to assume the generally arcuate shape, as shown in FIG. 10B. The distal portion 104 of the catheter 102 is positioned at the desired anatomical landmark, for example, the lower border of the noncoronary cusp of the aortic valve. The radiopaque marker 106 is on the distal-most section of the distal portion 104. In some embodiments of the method, the proximal end 114 of the catheter 102 is connected to a contrast material injector, and contrast material is injected into the lumen 118 of the catheter 102, for example to visualize the anatomy around the device 100. The contrast material exits the catheter 102 lumen 118 through the opening at the distal end 116 of the catheter 102 and/or through one or more apertures 108 in the side wall of the catheter 102. Injecting contrast material can aid in visualizing and positioning the catheter 102.

Figure 10C:
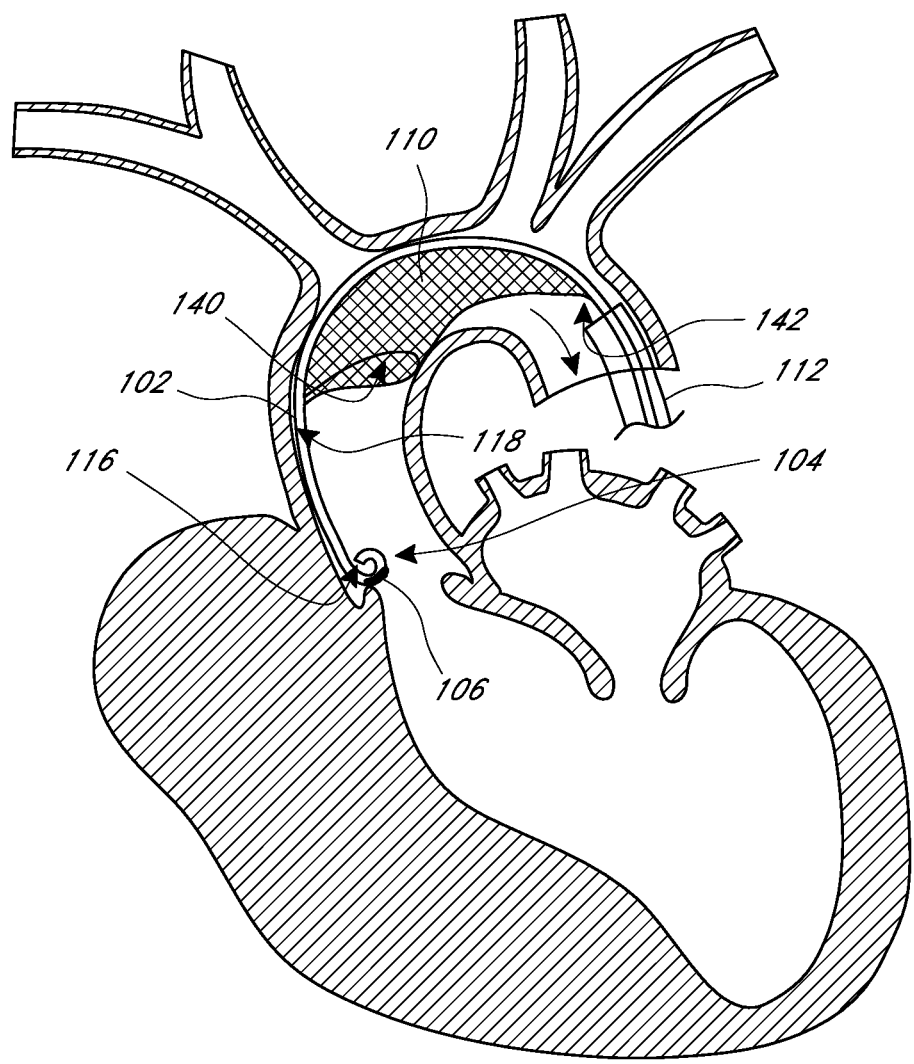

In some embodiments, a second guidewire is percutaneously inserted into a second body lumen, for example the other femoral artery, and a second catheter is tracked over the second guidewire. The second catheter can carry a medical device or instrument, for example, a replacement valve, a valve repair system, or a radio frequency ablation system. Once the second catheter and associated device or instrument are properly positioned, the outer sheath 112 of the catheter 102 is longitudinally proximally retracted, allowing the embolic filter 110 to assume the expanded, deployed configuration, as shown in FIG. 10C. The second guidewire and/or the second catheter can also be positioned after the embolic filter 112 is released. The open distal end 140 of the embolic filter 110 is located in the ascending aorta so that blood flows through the filter before flowing into the carotid arteries or descending aorta. In some embodiments, when the embolic filter 110 is deployed, the catheter 102 rests against the interior lumen wall, thereby stabilizing the catheter 102. The procedure can then be performed, and embolic debris dislodged or otherwise in the blood stream during the procedure is captured by the embolic filter 110.

Figure 10D:
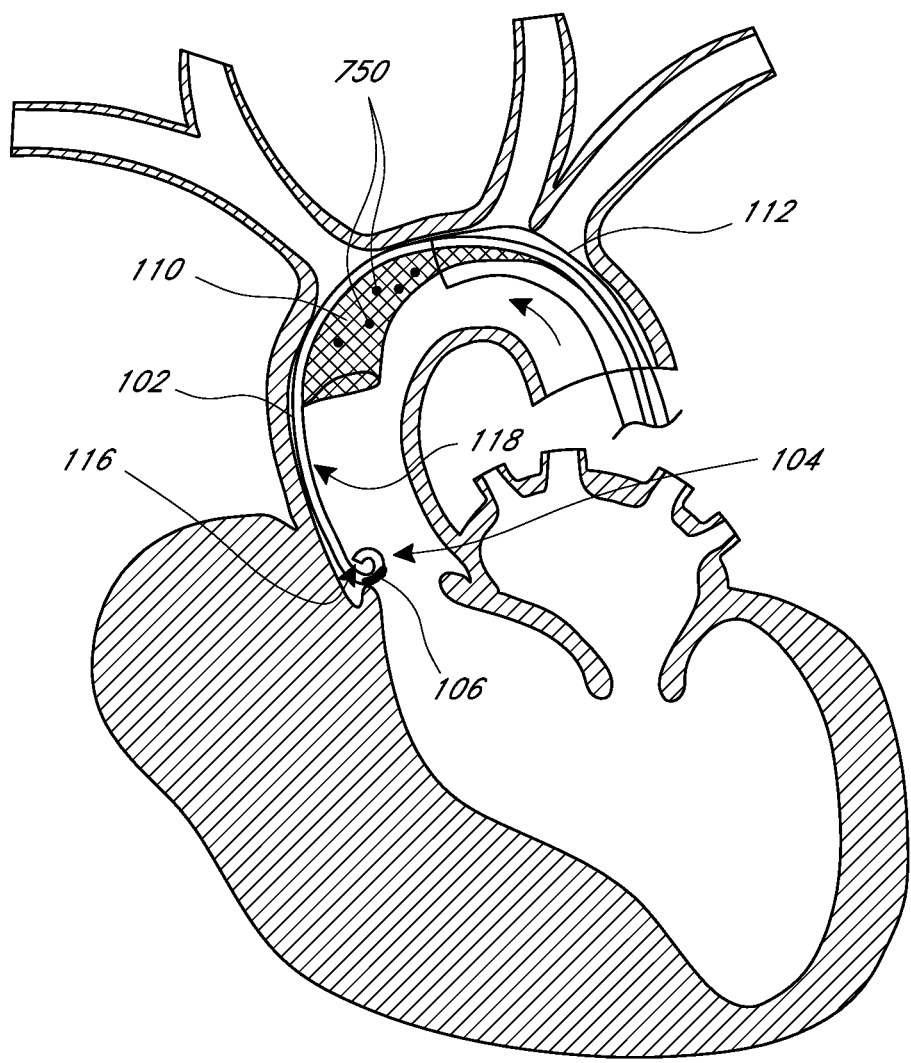

After the procedure, the outer sheath 112 is longitudinally distally advanced to recapture the embolic filter 110, returning the embolic filter 110 to the collapsed configuration and capturing any embolic debris 750 contained within the embolic filter 110, as shown in FIG. 10D. The second catheter and catheter 102 can then be withdrawn from the patient's body. The catheter 102 can be retracted over the guidewire 740 or without straightening the distal portion 104 of the catheter 102 because the arcuate shape of the distal portion 104 is atraumatic to the blood vessels.

Figure 11:
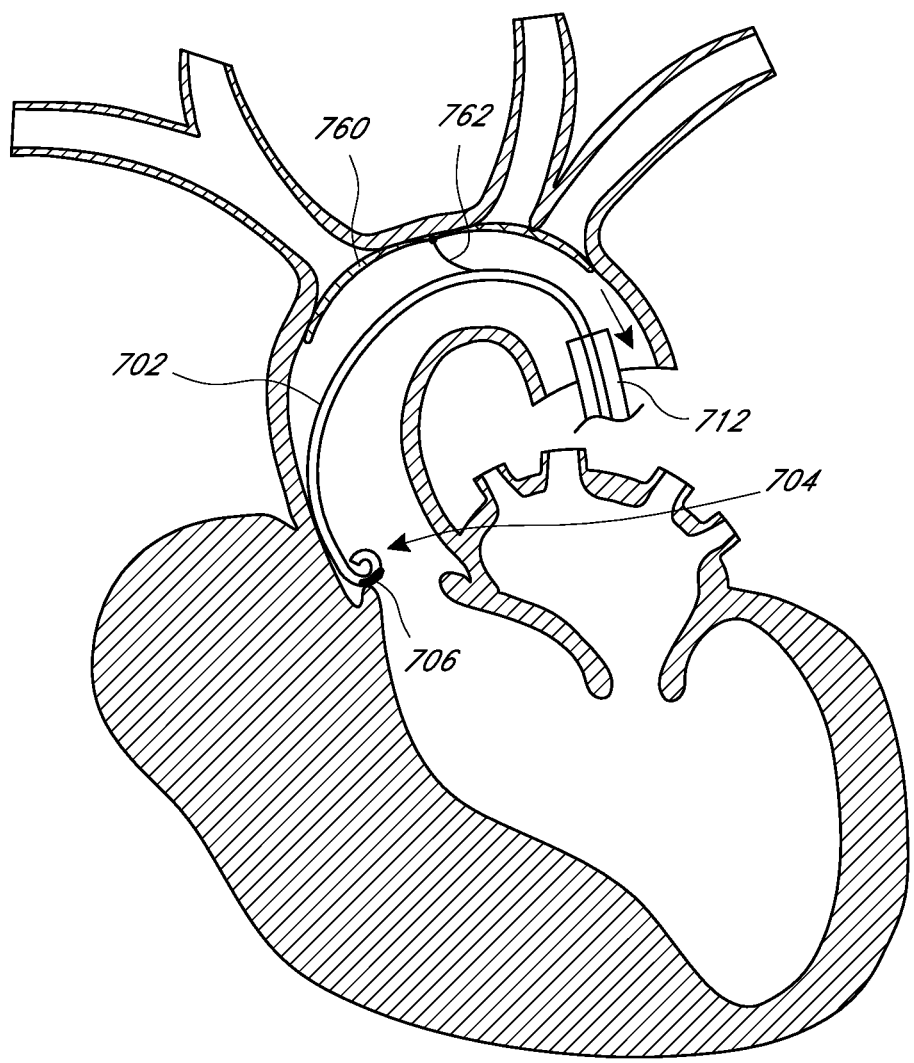
FIG. 11 shows an example embodiment of a method of deflecting embolic debris using an embolic protection device.

FIG. 11 illustrates an example embodiment of a method of deflecting embolic debris during a medical procedure, for example an aortic valve replacement procedure. The method can be performed using an embolic protection device 700 as described herein. The method is similar to the method performed using embolic protection device 100 illustrated in FIGS. 10A-10D and described herein. Once the pigtail catheter 702 and a second catheter with associated device or instrument are properly positioned, the longitudinal sheath 712 is longitudinally proximally retracted to deploy the deflector 760, as shown in FIG. 11. The deflector 760 spans the mouths or necks of the arteries branching off of the aortic arch so that blood entering those vessels flows through the deflector 760. The procedure can then be performed, and embolic debris dislodged or otherwise in the blood stream during the procedure is deflected away from the carotid arteries by the deflector 760. After the procedure, the outer sheath 712 is longitudinally distally advanced to recapture the deflector 760, returning the deflector 760 to the collapsed configuration. The second catheter and the catheter 702 can then be withdrawn from the patient's body.

Figure 12:
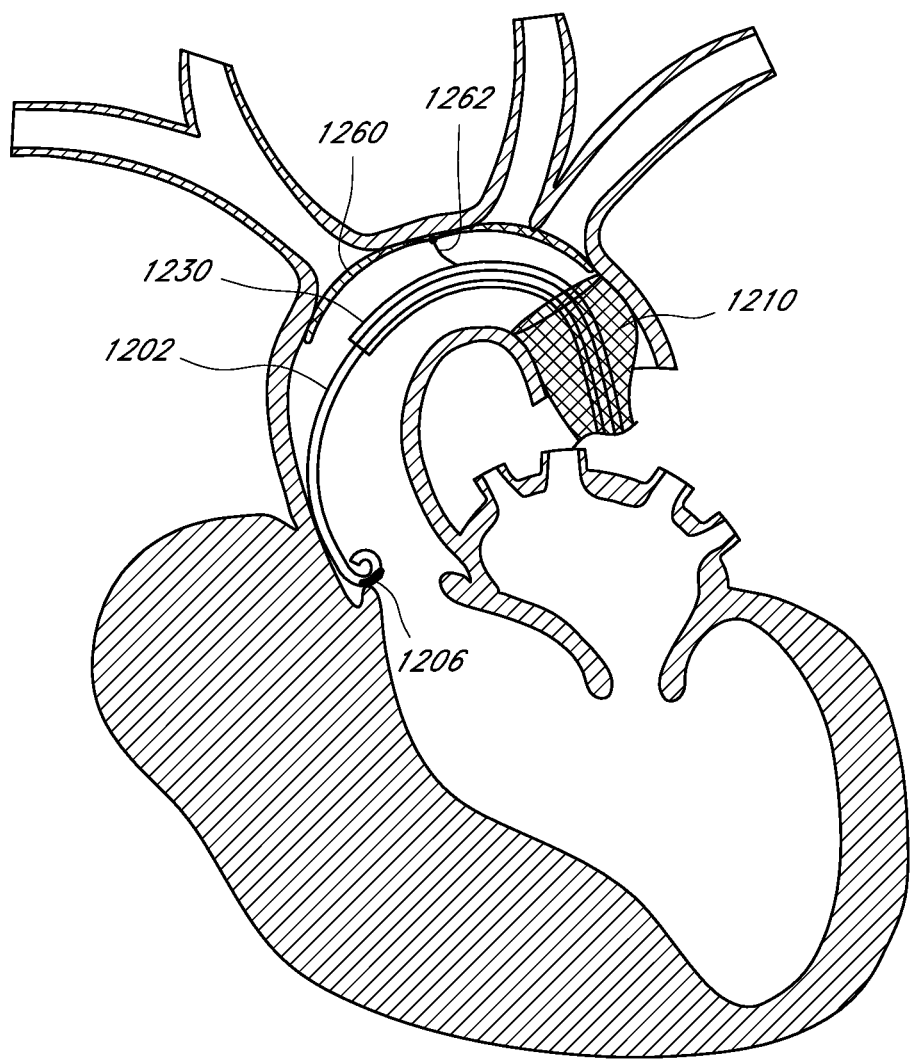
FIG. 12 shows another example embodiment of a method of deflecting embolic debris using an embolic protection device.

FIG. 12 illustrates another example embodiment of a method of deflecting and capturing embolic debris during a medical procedure using an embolic protection device. Certain aspects of the embolic protection device is similar to device 900 illustrated in FIG. 9 and described herein. The embolic filter 1210 is disposed around the catheter 1202 rather than coupled to a side of the catheter 1202, similar to embolic filter 610 illustrated in FIGS. 6A-6B and described herein. The deflector 1260 and embolic filter 1210 are also coupled to an intermediate tube 1230 that is longitudinally movable with respect to the catheter 1202, for example similar to embolic protection device 400 illustrated in FIGS. 4A-4D and described herein. The method is otherwise similar to the method using devices 100 and 700 as illustrated in FIGS. 10A-11 and described herein.

Figure 13:
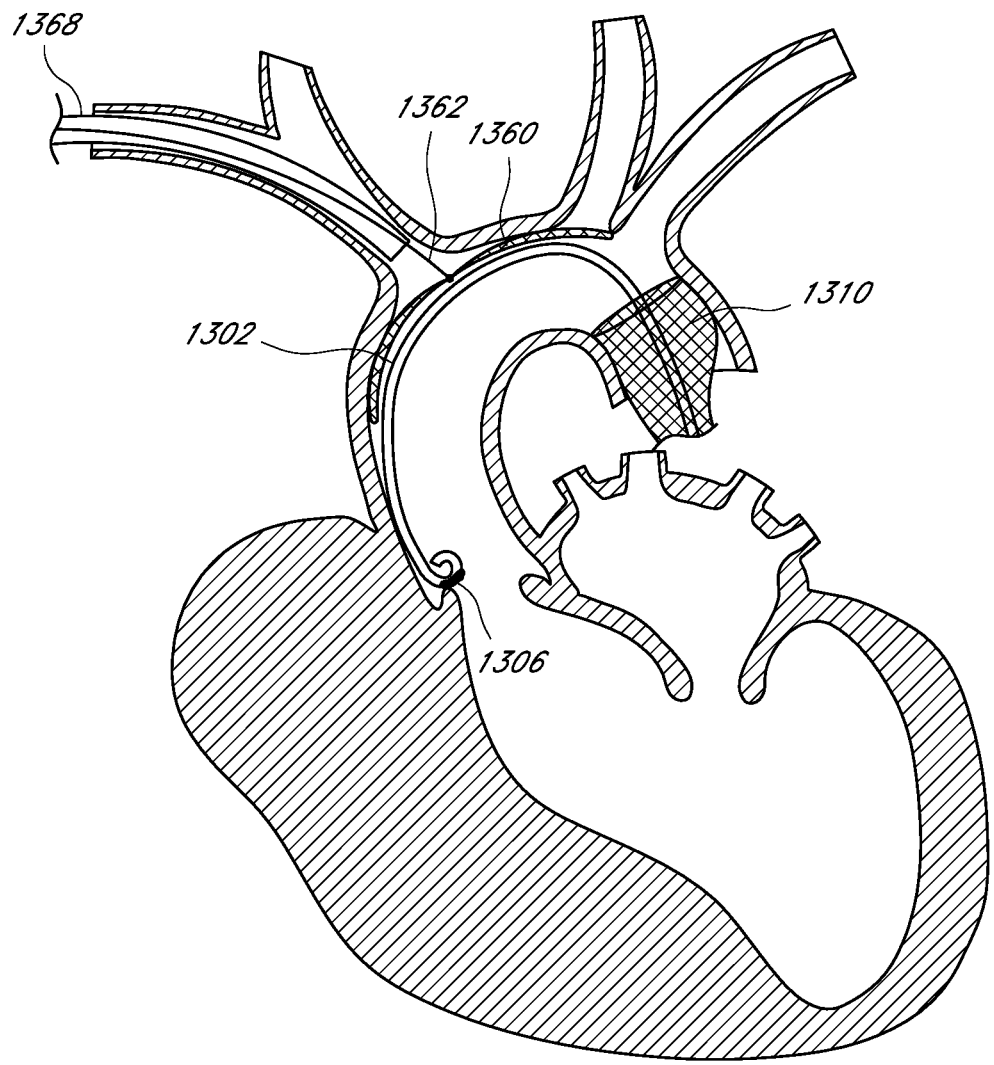
FIG. 13 shows an example embodiment of a method of deflecting and capturing embolic debris using an embolic protection device and deflector device.

Methods of deflecting and capturing embolic debris during a medical procedure can also be performed using an embolic protection device comprising an embolic filter as described herein and a separate deflector device. FIG. 13 illustrates an example embodiment of such a method. The embolic protection device of FIG. 13 comprises a pigtail catheter 1302 with a radiopaque marker 1306 and an embolic filter 1310 disposed around the catheter 1302 similar to embolic filter 610 illustrated in FIGS. 6A-6B and described herein. As shown, the deflector 1360 is mounted to a shaft 1362 and contained in an introducer 1368 during insertion. The introducer 1368 is introduced into the patient's body through the right radial artery and navigated to the aortic arch via the brachiocephalic artery. Once in position, the deflector 1360 is deployed from the introducer and pulled back to cover the brachiocephalic and left common carotid artery. In some patients, the deflector 1360 might also cover the left subclavian artery. In some embodiments, the deflector 1360 can be introduced and deployed before the catheter 1302 is navigated to the aortic arch. During a subsequent medical procedure, the deflector 1360 can prevent emboli from entering the carotid arteries, and the embolic filter 1310 can capture emboli deflected by the deflector 1360 before it travels to other parts of the patient's body. The method can also be performed with various other embolic protection devices, for example as described herein, and deflector devices that may vary in configuration and how they are introduced into the body and navigated to the aortic arch.

In some embodiments, the procedure performed is a cardiac valve replacement procedure, for example an aortic valve replacement procedure. The embolic protection device 100 is introduced into the patient and navigated to the aortic valve as described herein and shown in FIGS. 7A and 7B. The radiopaque marker 106 assists in delineating the lower border of the noncoronary cusp to assist in proper positioning of a percutaneously implanted replacement aortic valve. Once the catheter 102 is positioned, a second guidewire can be percutaneously inserted into a second body lumen and navigated to the level of the ascending aorta or left ventricle. A balloon can be tracked over the second guidewire to the aortic valve. The outer sheath 112 is then retracted to deploy the embolic filter 110. Balloon inflation of the valve can then be performed, and the embolic filter 110 captures embolic debris 750 dislodged during the procedure or otherwise in the blood stream. After balloon pre-dilation, the outer sheath 112 is advanced to recapture the embolic filter 110 and any embolic debris 750 contained within the embolic filter 110. The balloon is removed, and a second catheter carrying a valvular prosthesis is advanced to the level of the ascending aorta by tracking the catheter over the second guidewire. The outer sheath 112 is again retracted to redeploy the embolic filter 110. The radiopaque marker 106 allows the user to properly position the valve prosthesis, for example about 4 mm to about 6 mm below the lower border of the noncoronary cusp. After the procedure is completed, the outer sheath 112 is advanced to recapture the embolic filter 110 and any captured embolic debris 750, and the catheters are removed from the body. In some embodiments, the second catheter can be removed prior to advancing the outer sheath 112 to recapture the embolic filter 110 and embolic debris 750.

In some embodiments, the procedure is a cardiac valve repair procedure. The method described herein can also be adapted for a mitral valve repair or replacement procedure. In some embodiments, the procedure is a radio frequency ablation procedure, for example to treat atrial fibrillation. In some embodiments, the procedure is a catheterization procedure.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or subcombinations of the specific features and aspects of the embodiments may be made and still fall within the scope of the disclosure. It should be understood that various features and aspects of the disclosed embodiments can be combined with, or substituted for, one another in order to form varying modes of the embodiments of the disclosure. Furthermore, dimensions of various components provided herein are examples, and other dimensions may be used. Thus, it is intended that the scope of the disclosure herein should not be limited by the particular embodiments described above.

What is claimed is:

1. A method of capturing embolic debris during a closed heart surgical procedure, the method comprising:
   inserting a distal end of an angiography catheter into a first body lumen of a patient by tracking a lumen of the catheter over a guidewire percutaneously inserted into the first body lumen, the angiography catheter comprising:
      a proximal end and a distal end, the lumen extending from the proximal end to the distal end;
      a distal portion comprising a longitudinally-extending radiopaque marker;
      a self-expanding embolic filter attached to a side of the catheter proximal to the distal portion; and
      an outer sheath containing the embolic filter in a collapsed configuration;
   removing the guidewire from the lumen of the catheter, the distal portion of the catheter assuming a generally arcuate shape being at least a semi-circle upon removing the guidewire from the distal portion of the catheter;
   positioning the catheter by visualizing the radiopaque marker with an imaging technique; and
   longitudinally proximally retracting the outer sheath and allowing the embolic filter to assume an expanded, deployed configuration having a distal opening that faces the distal portion of the catheter and substantially spanning the body lumen,
   wherein the distal opening of the embolic filter faces the upstream direction of blood flow.

2. The method of claim 1, further comprising percutaneously inserting a second guidewire into a second body lumen of the patient and tracking a second catheter over the second guidewire, wherein the second catheter carries at least one of a replacement valve, a valve repair system, and a radio frequency ablation system.

3. The method of claim 2, further comprising positioning a distal end of the second catheter past the embolic filter of the angiography catheter.

4. The method of claim 3, further comprising at least partially advancing the outer sheath to narrow the distal opening of the embolic filter; and removing the second catheter from the second body lumen.

5. The method of claim 1, further comprising:
   longitudinally distally advancing the outer sheath, the embolic filter returning to the collapsed configuration and capturing any embolic debris contained in the embolic filter; and
   removing the angiography catheter from the first body lumen.

6. The method of claim 1, wherein positioning the angiography catheter comprises positioning the distal portion of the catheter against a lower border of a noncoronary cusp of an aortic valve.

7. The method of claim 1, further comprising connecting the proximal end of the angiography catheter to a contrast material injector.

8. The method of claim 1, wherein the shape of the distal opening of the embolic filter is elliptical; and wherein the distal opening of the embolic filter is attached to a self-expanding frame, and configured to self-expand to a radially expanded open configuration.

9. The method of claim 8, further comprising positioning the distal opening of the embolic filter in an ascending aorta upstream from a carotid artery.

10. The method of claim 1, further comprising longitudinally moving the embolic filter with respect to the angiography catheter.

11. The method of claim 1, wherein the angiography catheter further comprises a deflector; further comprising deploying the deflector.

12. An embolic protection device comprising:
    an angiography catheter having a proximal end, a distal end, and a lumen extending from the proximal end of the catheter to the distal end of the catheter, the lumen configured to house a guidewire, a distal portion of the catheter configured to assume a generally arcuate shape being at least a semi-circle;
    the distal portion of the catheter comprising a longitudinally-extending radiopaque marker configured to be arcuate and on a distal-most section of the catheter when the distal portion is in the generally arcuate shape;
    a self-expanding embolic filter coupled to a side of the catheter proximal to the distal portion, the embolic filter having a generally conical shape, the embolic filter comprising a distal opening having an elliptical shape and extending proximally from the distal opening to a closed proximal end;
    wherein the distal opening of the embolic filter faces the distal portion and is attached to a self-expanding frame configured to self-expand to a radially expanded open configuration; and
    a deployment mechanism circumferentially around at least a portion of the catheter and longitudinally movable with respect to the catheter, the deployment mechanism configured to contain the embolic filter in a collapsed configuration, and the embolic filter configured to self-expand upon longitudinal proximal retraction of the deployment mechanism.

13. The embolic protection device of claim 12, wherein the embolic filter comprises a braided nitinol mesh.

14. The embolic protection device of claim 12, wherein the embolic filter is movably coupled to the catheter and is longitudinally movable with respect to the catheter.

15. The embolic protection device of claim 14, wherein the embolic filter is moveably coupled to the catheter via an attachment to an intermediate tube coupled to the catheter wherein the intermediate tube at least partially circumferentially surrounds the catheter and is longitudinally moveable with respect to the catheter, wherein the deployment mechanism is configured to at least partially circumferentially surround both the catheter and the intermediate tube.

16. The embolic protection device of claim 14, further comprising a mechanism for determining the extent of movement of the deployment mechanism relative to the catheter to adjust the width of the distal opening.

17. The embolic protection device of claim 16, wherein the mechanism for determining the extent of movement of the deployment mechanism relative to the catheter comprises lips, shoulders, nubs, detents, or any combination thereof on the catheter, outer sheath, or both.

18. The embolic protection device of claim 12, wherein the generally arcuate shape of the distal portion is towards the side of the catheter to which the embolic filter is coupled.

19. The embolic protection device of claim 12, further comprising a self-expanding deflector coupled to the catheter proximal to the distal portion, the deflector having a longitudinal axis parallel to a longitudinal axis of the catheter.

20. The embolic protection device of claim 2, wherein the radiopaque marker is located on the outer curvature of the distal portion of the catheter when the distal portion assumes a generally arcuate shape.

21. The embolic protection device of claim 12, wherein the distal opening has a diameter of about 4.5 cm.

22. The embolic protection device of claim 12, wherein the embolic filter comprises a plurality of pores having a pore size of from about 40 microns to about 200 microns.

23. The embolic protection device of claim 12, wherein the embolic filter comprises a polyurethane membrane or a nitinol mesh.

24. The embolic protection device of claim 12, wherein the deployment mechanism comprises an outer sheath longitudinally movable with respect to the embolic filter, the outer sheath configured to contain the embolic filter in a collapsed state when at least partially around the embolic filter, and the embolic filter configured to self-expand upon longitudinal proximal retraction of the outer sheath.

25. The embolic protection device of claim 12, wherein the catheter has an outer diameter of from about 2 mm to about 3 mm.

26. The embolic protection device of claim 12, wherein the generally arcuate shape is at least 350 degrees.

* * * * *